(12) United States Patent
Kadowaki et al.

(10) Patent No.: US 7,583,578 B2
(45) Date of Patent: Sep. 1, 2009

(54) OPTICAL STORAGE MEDIUM INSPECTION METHOD FOR DETERMINING IF AN OPTICAL STORAGE MEDIUM IS GOOD OR DEFECTIVE

(75) Inventors: Shin-ichi Kadowaki, Sanda (JP); Mamoru Shoji, Sakai (JP); Atsushi Nakamura, Moriguchi (JP); Takashi Ishida, Yawata (JP)

(73) Assignee: Panasonic Corporation, Osaka (JP)

( * ) Notice: Subject to any disclaimer, the term of this patent is extended or adjusted under 35 U.S.C. 154(b) by 55 days.

(21) Appl. No.: 11/980,662

(22) Filed: Oct. 31, 2007

(65) Prior Publication Data

US 2008/0247290 A1 Oct. 9, 2008

Related U.S. Application Data

(62) Division of application No. 10/509,740, filed as application No. PCT/JP03/04209 on Apr. 2, 2003.

(30) Foreign Application Priority Data

| Apr. 3, 2002 | (JP) | ............................ P2002-100961 |
| May 27, 2002 | (JP) | ............................ P2002-152904 |
| Jul. 26, 2002 | (JP) | ............................ P2002-217856 |

(51) Int. Cl.
*G11B 7/00* (2006.01)

(52) U.S. Cl. .................................. 369/53.34; 369/59.19

(58) Field of Classification Search ........................ None
See application file for complete search history.

(56) References Cited

U.S. PATENT DOCUMENTS 5,675,565 A   10/1997  Taguchi et al.

6,252,835 B1   6/2001   Choi
6,366,631 B1   4/2002   Nakayama et al.
6,492,915 B2  12/2002   Maeda et al.

(Continued)

FOREIGN PATENT DOCUMENTS

EP          0 987 697          3/2000

(Continued)

OTHER PUBLICATIONS

U.S. Office Action issued Aug. 7, 2008 in U.S. Appl. No. 10/509,740.

(Continued)

*Primary Examiner*—Peter Vincent Agustin
(74) *Attorney, Agent, or Firm*—Wenderoth, Lind & Ponack, L.L.P.

(57) ABSTRACT

An optical disc drive having an optical pickup head emitting a light beam to an optical storage medium, detecting the light beam reflected from the optical storage medium, and outputting a signal based on the received reflected light, having a jitter measuring unit measuring jitter in signals output from the optical pickup head and having an evaluation unit determining from the measured jitter if the optical storage medium is good or defective. The jitter measuring unit measures jitter in a train of 3T or longer marks or spaces from an optical storage medium to which digital information is recorded as a train of marks or spaces of length kT based on a period T and an integer k of two or more.

1 Claim, 27 Drawing Sheets

U.S. PATENT DOCUMENTS

| | | |
|---|---|---|
| 6,665,250 B1 | 12/2003 | Minamino et al. |
| 6,731,578 B1 | 5/2004 | Sako et al. |
| 6,791,926 B1 | 9/2004 | Furumiya et al. |
| 7,170,835 B1 | 1/2007 | Roh et al. |
| 2001/0055169 A1 | 12/2001 | Noda et al. |
| 2002/0159345 A1 | 10/2002 | Mashimo et al. |
| 2003/0053386 A1 | 3/2003 | Takeda |
| 2003/0185128 A1 | 10/2003 | Shoji et al. |

FOREIGN PATENT DOCUMENTS

| | | |
|---|---|---|
| EP | 1 059 630 | 12/2000 |
| EP | 1 229 538 | 8/2002 |
| JP | 8-124161 | 5/1996 |
| JP | 2001-291325 | 10/2001 |
| JP | 2002-237036 | 8/2002 |
| KR | 2001-0033848 | 5/2000 |
| KR | 2001-0072819 | 1/2001 |
| WO | 00/28535 | 5/2000 |
| WO | 01/33568 | 5/2001 |
| WO | 02/25645 | 3/2002 |

OTHER PUBLICATIONS

International Search Report issued in the International (PCT) Application of which the present application is the U.S. National Stage, mailed Jul. 22, 2003.

Supplementary European Search Report issued Dec. 5, 2006 in European Application EP 03 71 5724.

ABSTRACT# OPTICAL STORAGE MEDIUM INSPECTION METHOD FOR DETERMINING IF AN OPTICAL STORAGE MEDIUM IS GOOD OR DEFECTIVE

This application is a divisional of U.S. application Ser. No. 10/509,740, filed Jul. 26, 2005, which is a national stage application of International Application No. PCT/JP03/04209, filed Apr. 2, 2003.

BACKGROUND OF THE INVENTION

1. Field of the Invention

The present invention relates to an optical storage medium for recording information using marks and spaces, an optical disc drive for recording, reading, or deleting data on the optical storage medium, an optical storage medium inspection apparatus for determining whether the optical storage medium is good or defective, and an optical storage medium inspection method for determining whether the optical storage medium is good or defective.

2. Description of the Related Art

High density, high capacity optical storage media known as DVD, or Digital Versatile Disc, have been developed as a practical high density, high capacity storage medium, and are today widely used as a data medium for handling video and other such large amounts of information. Development of two-layer optical storage media capable of recording to two data recording layers has also been reported by various manufacturers as a means of achieving optical storage media with even greater storage capacity. Development of means for recording as well as reading large amounts of data is also progressing on many fronts with various approaches being used to achieve increasingly higher recording densities. One such approach is the phase-change optical disc drive using a reversible phase change between crystalline and amorphous states.

Japanese Patent Laid-Open Publication No. 2000-200418 teaches technology for recording and reading data by emitting a beam to a phase-change optical storage medium.

FIG. 20 shows the configuration of a common optical system used in the optical pickup head of an optical recording and playback system as an optical disc drive capable of reading and writing data. The semiconductor laser 1 light source emits a linearly polarized divergent beam 70 with an oscillation wavelength λ1 of 405 nm. The divergent beam 70 emitted from semiconductor laser 1 is converted to parallel light by a collimating lens 53 with a 15 mm focal length, and is then incident to a diffraction grating 58. The divergent beam 70 incident to the diffraction grating 58 is split into three beams of orders 0 and +/−1 diffracted light. The order 0 diffracted light is the main beam 70a for data recording and playback, and the order +/−1 diffracted beams are the two sub-beams 70b and 70c used when detecting the tracking error (TE) signal by a differential push-pull (DPP) method for stably detecting the TE signal. The diffraction efficiency ratio of the diffraction grating between the zero order beam and one first order beam is normally set from 10:1 to 20:1 in order to avoid unwanted recording by sub-beams 70b and 70c, and is here assumed to be 20:1. The three beams produced by the diffraction grating 58, that is, main beam 70a and sub-beams 70b and 70c, pass polarized beam splitter 52, ¼ wave plate 54, and are converted to circular polarized light which is then converted to a convergent beam by objective lens 56 with a 3 mm focal length and focused on the data recording layer 40b through transparent layer 40a of the optical storage medium 40. The aperture of the objective lens 56 is limited by aperture 55 to a 0.85 numerical aperture (NA). The transparent layer 40a is 0.1 mm thick. The optical storage medium 40 has a data recording layer 40b and transparent layer 40a. The data recording layer 40b is a semi-transparent film and only part of the incident beam passes. The beam that passes the data recording layer 40b is used for reading and writing data to data recording layer 40c.

FIG. 25 shows the track configuration of an optical storage medium 40 according to the prior art. This optical storage medium 40 is an optical storage medium having a recording area in a groove-shaped track (groove track 1301) with the groove track formed in a continuous spiral.

FIG. 21 shows the relationship between a beam and the track on the data recording layer 40b. A continuous groove is formed as the tracks, identified as tracks Tn−1, Tn, Tn+1, of the optical storage medium 40. The track period Tp is 0.32 μm. The laser beam is positioned so that when the main beam 70a is on a track, sub-beams 70b and 70c are between tracks. That is, the distance L between the main beam and sub-beams in the direction orthogonal to the track is 0.16 μm. As with DVD media, data is recorded using 8-16 modulation, that is, using marks and spaces having a length that is an integer multiple of T based on period T where the length of the shortest mark and the length of the shortest space is each 3T. The shortest mark length is 0.185 μm.

The main beam 70a and sub-beams 70b and 70c reflected by the data recording layer 40b pass objective lens 56 and ¼ wave plate 54, are converted to linear polarized light 90 degrees to the incoming path, and reflected by the polarized beam splitter 52. The main beam 70a and sub-beams 70b and 70c reflected by the polarized beam splitter 52 are converted to convergent light as they pass through collective lens 59, pass cylindrical lens 57 and are incident to photodetector 32. Astigmatic aberration is added to main beam 70a and sub-beams 70b and 70c when they pass cylindrical lens 57.

As shown in FIG. 22, the photodetector 32 has eight receptors 32a to 32h with receptors 32a to 32d detecting the main beam 70a, receptors 32e, 32f detecting sub-beam 70b, and receptors 32g, 32h detecting sub-beam 70c. Receptors 32a to 32h respectively output current signals I32a to I32h according to the detected light quantity.

The focus error (FE) signal from the astigmatic aberration method is obtained as (I32a+I32c)−(I32b+I32d).

The TE signal from the DPP method is obtained as $\{(I32a+I32c)-(I32b+I32d)\}-a*\{(I32e-I32f)+(I32g-I32h)\}$ where a is a coefficient dependent on the diffraction efficiency of the diffraction grating and is here 10.

The data (RF) signal recorded to the optical storage medium 40 is

I32a+I32b+I32c+I32d.

After amplification to a desired level and phase compensation, the FE signal and TE signal are supplied to actuators 91 and 92 for focusing and tracking control.

The eye pattern of the RF signal is shown in FIG. 23. The data recorded to optical storage medium 40 is obtained by inputting the RF signal to a transversal filter and emphasizing the high frequency band, digitizing the signal, and then demodulating the digital signal. Because 8-16 modulation produces DC-free code, the binarization threshold value SL can be easily set to the center of the eye by integrating the 1s and 0s of the binarized signal by time and applying a differential operation.

A phase-change type optical disc drive emits a semiconductor laser to the optical storage medium using two power levels, a peak power level for changing the recording layer from crystalline phase to amorphous phase, and a bias power level for changing it from amorphous phase to crystalline phase, thereby forming amorphous marks on the optical storage medium and crystalline spaces between the marks to record digital information. The reflectivity of these marks and spaces differs due to the difference of the crystalline state of the marks and spaces, and this difference in reflectivity is used during playback to read the recorded signal.

FIG. 24 shows the configuration of a phase-change type optical disc drive according to the prior art. As shown in FIG. 24 this optical disc drive has an optical pickup head 1202 for emitting a laser beam to the optical storage medium 40 and receiving light reflected from the optical storage medium 40, a playback means 1203, playback signal quality detector 1204, optimal recording power determination means 1205, recording means 1208, laser drive circuit 1207, and recording power determination means 1206.

After the optical storage medium 40 is loaded in the optical disc drive and specific operations for identifying the media type and rotation control are completed, the optical pickup head 1202 moves to an area for setting the optimal recording power. This area is a predetermined area at the inside or outside circumference of the disc outside of the user area where user data is recorded. The peak, bias, and bottom power levels are determined for phase-change media, but a method for determining the peak power is described here.

Initial peak power and bias power levels are set in the laser drive circuit 1207 by the recording power determination means 1206. The recording means 1208 then sends a signal for recording one groove track to the laser drive circuit 1207, and the signal is recorded by the optical pickup head 1202. The output beam of the semiconductor laser part of the optical pickup head 1202 is focused as a light spot on the optical storage medium 40 at this time to form a recording mark according to the beam emission waveform. When recording is completed the semiconductor laser of the optical pickup head 1202 emits at the read power level to play back the track that was just recorded, and a signal 1209 that varies according to the presence of these recording marks on the optical storage medium 40 is input as the playback signal to the playback means 1203. A playback signal process including amplification, equalization, and digitizing is then applied to this playback signal 1209 by the playback means 1203, and the resulting signal 1210 is input to the playback signal quality detector 1204.

The playback signal quality detector 1204 detects the signal quality of signal 1210 and the result is input to the optimal recording power determination means 1205.

In this example the playback signal quality detector 1204 detects jitter when the recorded signal is reproduced. FIG. 26 shows the relationship between peak power and jitter. Peak power is shown on the horizontal axis and jitter on the vertical axis in FIG. 26. If the playback conditions are equal, a lower jitter level indicates accurate recording. The detection result, i.e., signal quality, is therefore determined OK if jitter is less than or equal to a set threshold value, and no good (NG) if above this threshold value.

The optimal recording power determination means 1205 operates according to a flow chart such as shown in FIG. 27.

(a) If the first result of the playback signal quality detector 1204 is NG, the peak power is reset to a level higher than the initial setting (step 1505).

(b) If the result of the playback signal quality detector 1204 is OK, the peak power is reset to a level lower than the initial setting (step 1504).

(c) The groove track is again recorded at the set peak power level and then read (step 1506).

(d) If the first result from the playback signal quality detector 1204 is NG and the second result is OK, the optimal recording power determination means 1205 sets the optimal recording power to the average of the current peak power setting and the previous peak power setting plus a specified margin (step 1511).

(e) If the first result from the playback signal quality detector 1204 is OK and the second result is NG, the optimal recording power determination means 1205 sets the optimal recording power to the average of the current peak power setting and the previous peak power setting plus a specified margin (step 1511).

With the conventional configuration described above, however, the I3 pp/I4 pp ratio between the signals obtained from data recording layers 40b and 40c is 15% and 20% and jitter is 10% and 8%, respectively, and in each case the characteristics of signals read from data recording layer 40b are worse than those of signals read from data recording layer 40c. This means that recorded data cannot be read with high reliability unless the recording density of data recorded to data recording layer 40b is lower than the recording density of data recorded to data recording layer 40c.

Furthermore, the area for determining the optimum emission power is generally different from the user area for recording user data. As a result, warping of the optical storage medium and variations in pickup head installation can produce a relative tilt between these two areas, and user data may be recorded at a lower effective power level than the emission power determined in the area for determining the optimum recording power. Conversely, user data may be recorded at a higher effective power level than the emission power determined in the area for determining the optimum recording power. The prior art described above determines the optimum power level based on the jitter detected after recording a random signal, but because the signal quality of the shortest mark has the greatest effect on jitter, the optimal power level for the shortest marks is actually determined. While data can therefore be correctly recorded with the shortest marks even if the recording power fluctuates somewhat, the effect of power fluctuation cannot be ignored for marks longer than the shortest marks particularly if the recording density increases, and recorded signal quality can deteriorate.

Furthermore, if relative tilt between the optical storage medium and head or defocusing occurs during playback, the playback signal quality drops for signals read from marks longer than the shortest mark, and it may not be possible to correctly reproduce the data.

The present invention is directed to solving these problems of the conventional optical disc drive, and a first object of the invention is to provide an optical storage medium and optical disc drive that can record or reproduce data with high reliability even when the data recording density is the same on two data recording layers.

A second object of the invention is to provide an optical storage medium and optical disc drive that can record or reproduce data with high reliability even using an optical storage medium in which jitter from the shortest marks and spaces is worse than jitter from marks and spaces longer than the shortest marks and spaces.

A third object of the invention is to provide an optical storage medium and optical disc drive that can correctly record or reproduce data even when defocusing or relative tilt between the optical pickup head and optical storage medium occurs during recording or playback.

SUMMARY OF THE INVENTION

An optical storage medium inspection apparatus according to the present invention comprises an optical pickup head that emits a light beam to an optical storage medium, detects a light beam reflected from the optical storage medium, and outputs a signal based on the received reflected light;

a jitter measuring unit for measuring jitter in signals output from the optical pickup head; and an evaluation unit for determining from the measured jitter if the optical storage medium is good or defective;

wherein the jitter measuring unit measures jitter in a train of 3T or longer marks or spaces from an optical storage medium to which digital information is recorded as a train of marks or spaces of length kT based on a period T and an integer k of two or more. The above object is thereby achieved.

Another optical storage medium inspection apparatus according to the present invention comprises an optical pickup head that emits a light beam to an optical storage medium, detects a light beam reflected from the optical storage medium, and outputs a signal based on the received reflected light;

a jitter measuring unit for measuring jitter in signals output from the optical pickup head; and an evaluation unit for determining from the measured jitter if the optical storage medium is good or defective;

wherein the jitter measuring unit measures jitter from an optical storage medium to which digital information is recorded as a train of marks or spaces of length kT based on a period T and an integer k of two or more, but does not measure jitter in signals obtained from edges of marks or spaces of length 2T. The above object is thereby achieved.

The above-described optical disc drive preferably measures jitter from an optical storage medium on which the width of 2T-long marks is narrower than the width of marks longer than 2T.

Further preferably, l2 pp/l8 pp <0.2 where l2 pp is a signal reproduced from a pattern repeatedly recording 2T-long digital data marks and spaces and l8 pp is a signal reproduced from a pattern repeatedly recording 8T-long digital data marks and spaces.

Yet further preferably, $ML<\lambda/(1.25*NA)$ where ML is the length of a pair of digital data marks and spaces of length 2T, $\lambda$ is the wavelength of the light beam emitted from the optical pickup head, and NA is the numeric aperture of the collector optics of the optical pickup head.

The jitter measuring unit could measure jitter from an optical storage medium having a first recording layer formed from a semi-transparent film that passes part of light incident thereon and a second recording layer. The jitter measuring unit measures jitter in a signal obtained from the second recording layer when the part of the light reaches the second recording layer through the first recording layer.

Yet further preferably, a gain adjustment means for reducing variation in the amplitude of signals input to a demodulation means when reflectivity of the optical storage medium varies is also provided.

An optical storage medium inspection method according to the present invention is a method for determining if an optical storage medium is good or defective, the method comprising the steps of:

emitting a light beam from an optical pickup head to the optical storage medium to which digital information is recorded as a train of marks or spaces of length kT based on a period T and an integer k;

receiving light reflected by a mark or space;

measuring jitter in signals based on the reflected light, but not measuring jitter in signals obtained from edges of the shortest marks or spaces; and determining from the measured jitter whether the optical storage medium is good or defective. The above object is thereby achieved.

Preferably, the marks or spaces of the shortest length are marks or spaces of length 2T, and jitter is measured except for jitter in signals obtained from the edges of digital data marks or spaces of length 2T.

Another optical disc drive according to the present invention comprises an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium using maximum likelihood decoding. The optical storage medium has a recording layer for recording data. Digital data of length kT based on a period T is recorded as a mark or space sequence to the recording layer, k is an integer of 2 or more, and the width of a 2T long digital data mark is narrower than the width of a digital data mark longer than 2T. The above object is thereby achieved.

Yet another optical disc drive according to the present invention comprises an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium using two threshold values. The optical storage medium has a first recording layer and a second recording layer. The first recording layer is a semi-transparent layer that passes part of the light incident thereon, light passing the first recording layer reaches the second recording layer, and digital data of length kT based on a period T is recorded as a mark or space sequence to the first recording layer, k being an integer of 2 or more. The above object is thereby achieved.

Yet another optical disc drive according to the present invention comprises an optical disc drive having an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium using maximum likelihood decoding. The optical storage medium has a first recording layer and a second recording layer. The first recording layer is a semi-transparent layer that passes part of the light incident thereon; light passing the first recording layer reaches the second recording layer, and digital data of length kT based on a period T is recorded as a mark or space sequence to the first recording layer, k being an integer of 2 or more. The above object is thereby achieved.

Yet another optical disc drive according to the present invention comprises an optical pickup head that emits a light beam to the optical storage medium, detects the light beam reflected from the optical storage medium, and outputs a signal based on the received reflected light; a clock generating means for receiving signals output from the optical pickup head and extracting digital information recorded to the optical storage medium; and a demodulation means that reproduces data recorded to the optical storage medium. The optical storage medium has a first recording layer and a second recording layer. The first recording layer is a semi-transparent layer that passes part of the light incident thereon; light passing the first recording layer reaches the second recording layer, and digital data of length kT based on a period T is recorded as a mark or space sequence to the first recording layer, k being an integer of 2 or more. The clock generating means generates a clock signal by treating as invalid signals obtained from the edges of 2T digital data marks or spaces. The above object is thereby achieved.

Yet another optical disc drive according to the present invention comprises an optical pickup head that emits a light beam to the optical storage medium, detects the light beam reflected from the optical storage medium, and outputs a signal based on the received reflected light; a clock generating means for receiving signals output from the optical pickup head and extracting digital information recorded to the optical storage medium; and a demodulation means that reproduces data recorded to the optical storage medium. The optical storage medium has a recording layer. Digital data of length kT based on a period T is recorded as a mark or space sequence to the recording layer, k is an integer of 2 or more, and the width of a 2T digital data mark is narrower than the width of a digital data mark longer than 2T. The clock generating means generates a clock signal by treating as invalid signals obtained from the edges of 2T digital data marks or spaces. The above object is thereby achieved.

Yet another optical disc drive according to the present invention comprises an optical pickup head that emits a light beam to the optical storage medium, detects the light beam reflected from the optical storage medium, and outputs a signal based on the received reflected light; a clock generating means for receiving signals output from the optical pickup head and extracting digital information recorded to the optical storage medium; a demodulation means that reproduces data recorded to the optical storage medium; and a TE signal generating means used for tracking control. The optical storage medium has a recording layer. Digital data of length kT based on a period T is recorded as a mark or space sequence to the recording layer, k being an integer of 2 or more. The tracking error signal generating means generates a tracking error signal from change in the signals produced when the light beam strikes the edges of the mark or space sequence recorded to the optical storage medium, and generates the tracking error signal by invalidating signal change resulting from the light beam at the edges of 2T-long digital data marks or spaces. The above object is thereby achieved.

In the above optical disc drive the recording layer preferably enables repeatedly recording and erasing information.

Furthermore, the recording layer could enable recording data only once.

Furthermore, the recording layer could be read-only.

Furthermore, the first recording layer could be read-only and the second recording layer could enable recording data only once.

Furthermore, the first recording layer could be read-only and the second recording layer could enable recording and erasing data multiple times.

Yet another optical disc drive according to the present invention comprises an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium. The optical storage medium has a recording layer for recording data. Digital data of length kT based on a period T is recorded as a mark or space sequence to the recording layer, k is an integer of 2 or more, and the width of a 2T digital data mark is narrower than the width of a 3T or longer digital data mark. The optical disc drive adjusts the length of a 2T digital data mark so that the length detected from a pattern repeatedly recording 2T-long digital data marks and spaces goes to the same level as a threshold value suitable for reproducing information in a pattern repeatedly recording 3T or longer digital data marks and spaces. The above object is thereby achieved.

Yet another optical disc drive according to the present invention comprises an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium. The optical storage medium has a recording layer for recording data. Digital data of length kT based on a period T is recorded as a mark or space sequence to the recording layer, and k is an integer of 2 or more. The optical disc drive has an evaluation standard so that mark and space length is appropriate, and adjusts the length of digital data marks and spaces longer than 2T so that the length is appropriate relative to the evaluation standard. The above object is thereby achieved.

Yet another optical disc drive according to the present invention comprises an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium. The optical storage medium has a recording layer for recording data, and digital data of length kT based on a period T is recorded as a mark or space sequence to the recording layer using an evaluation standard for adjusting mark and space length to an appropriate length. When recording to an optical storage medium that is normally recorded with k being an integer of 2 or more, the optical disc drive records information using a k of 3 or more, and adjusts the length of digital data marks and spaces of length 3T or more so that the length is appropriate relative to the evaluation standard. The above object is thereby achieved.

The evaluation standard in this optical disc drive is preferably jitter.

Furthermore, the evaluation standard could be an error rate.

Furthermore, the evaluation standard could be the time period of an obtained signal.

Further preferably, mark length could be adjusted by adjusting the power of the laser beam emitted from the optical pickup head.

Further preferably, mark length could be adjusted by adjusting the pulse width of the laser beam emitted from the optical pickup head.

Further preferably, jitter is measured from an optical storage medium where the width of 2T-long digital data marks is narrower than the width of digital data marks longer than 2T.

Further preferably, jitter is measured in a signal obtained by emitting a light beam to the first recording layer of an optical storage medium having a first recording layer and a second recording layer, the first recording layer being a semi-transparent film that passes part of the light incident thereon, the light passing the first recording layer reaching the second recording layer.

Further preferably, I2 pp/I8 pp<0.2 where I2 pp is a signal reproduced from a pattern repeatedly recording 2T-long digital data marks and spaces and I8 pp is a signal reproduced from a pattern repeatedly recording 8T-long digital data marks and spaces.

Further preferably, ML<λ/(1.25*NA) where ML is the length of a pair of digital data marks and spaces of length 2T, λ is the wavelength of the light beam emitted from the optical pickup head, and NA is the numeric aperture of the collector optics of the optical pickup head.

Further preferably, the optical disc drive also has a gain adjustment means so that variation in the amplitude of signals input to the demodulation means is small when the reflectivity of the optical storage medium varies.

An optical storage medium according to the present invention is an optical storage medium whereby information is recorded or reproduced by exposure to a light beam, the optical storage medium having a first recording layer and a second recording layer as recording layers for recording information, the first recording layer being a read-only recording layer, the second recording layer being a recording layer enabling recording data only once, and the first recording layer being disposed closer to the light incidence side of the medium than the second recording layer. The above object is thereby achieved.

Another optical storage medium according to the present invention is an optical storage medium whereby information is recorded or reproduced by exposure to a light beam, the optical storage medium having a first recording layer and a second recording layer as recording layers for recording information, the first recording layer being a read-only recording layer, the second recording layer being a recording layer enabling repeatedly recording and erasing data, and the first recording layer being disposed closer to the light incidence side of the medium than the second recording layer. The above object is thereby achieved.

Another optical storage medium according to the present invention is an optical storage medium having multiple tracks formed concentrically or in a spiral for recording information using marks and spaces between the marks by emitting a light beam to the recording surface of the tracks, and is characterized by a signal not including edges adjacent to the shortest marks and/or the shortest spaces denoting a first playback signal quality. The above object is thereby achieved.

Preferably, the optical storage medium also has a signal including edges adjacent to the shortest marks and/or the shortest spaces denoting a second playback signal quality.

Furthermore, the first playback signal quality is preferably higher than the second playback signal quality.

Furthermore, jitter can be detected as the playback signal quality.

Furthermore, leading-edge jitter and trailing-edge jitter can be separately detected.

An error rate could also be detected as the playback signal quality.

The optical storage medium could also have multiple recording layers with playback signal quality set for each layer.

Furthermore, during recording the quality of the layer farthest from the optical pickup head could be highest. The playback signal quality threshold value could also be written to a specific area of the optical storage medium.

This specific area is preferably a read-only area.

Further preferably, signals are also recorded to tracks adjacent to a track having a specified playback signal quality.

Furthermore, the track having a specified playback signal quality could be recorded before the adjacent tracks are recorded.

Furthermore, the emission power of the laser beam when recording the adjacent tracks can be greater than the emission power of the laser beam when recording the track having a specified playback signal quality.

Furthermore, the track having a specified playback signal quality could be recorded after recording to one adjacent track.

Furthermore, the track having a specified playback signal quality could be recorded after recording to both adjacent tracks.

Furthermore, the track having a specified playback signal quality could be recorded multiple times.

Yet further preferably, playback signal quality is a specified level in all of a specific number of recordings.

Furthermore, the optical storage medium is recorded at a second emission power level after recording at a first emission power level, the first emission power level being higher than the second emission power level.

An optical disc drive according to the present invention is an optical disc drive for reading an optical storage medium having multiple tracks formed concentrically or in a spiral for recording information using marks and spaces between the marks by emitting a light beam to the recording surface of the tracks, the optical storage medium having a first playback signal quality denoted by a signal not including edges adjacent to the shortest marks and/or the shortest spaces. The above object is thereby achieved.

An optical disc drive according to the present invention is an optical disc drive for reading an optical storage medium having multiple tracks formed concentrically or in a spiral for recording information using marks and spaces between the marks by emitting a light beam to the recording surface of the tracks, the optical storage medium having a first playback signal quality denoted by a signal not including edges adjacent to the shortest marks and/or the shortest spaces, and a second playback signal quality denoted by a signal including edges adjacent to the shortest marks and/or the shortest spaces. The above object is thereby achieved.

An optical disc drive according to the present invention is an optical disc drive for recording so that a signal not including edges adjacent to the shortest marks and/or the shortest spaces has a first playback signal quality, the optical disc drive comprising means for recording a signal, means for reproducing the recorded signal, means for detecting a shortest mark or a shortest space in the reproduced signal, and a playback signal quality detection means for detecting playback signal quality in a signal not including edges adjacent to the detected shortest mark or shortest space. The above object is thereby achieved.

Preferably, a signal including edges adjacent to the shortest marks and/or the shortest spaces denotes a second playback signal quality.

Further preferably, the first playback signal quality is higher than the second playback signal quality.

Further preferably, jitter is detected to determine the playback signal quality.

Further preferably, leading-edge jitter and trailing-edge jitter are separately detected.

The error rate could also be detected to determine playback signal quality.

Further preferably, the optical storage medium has multiple recording layers and playback signal quality is set for each recording layer.

Further preferably, the quality of the layer farthest from the optical pickup head is highest during recording.

Further preferably, the playback signal quality threshold value is written to a specific area of the optical disc drive.

Furthermore, signals could also be recorded to tracks adjacent to a track having a specified playback signal quality.

Furthermore, the track having a specified playback signal quality can be recorded before recording to the adjacent tracks.

Furthermore, the emission power of the laser beam when recording the adjacent tracks can be greater than the emission power of the laser beam when recording the track having a specified playback signal quality.

Furthermore, the track having a specified playback signal quality can be recorded after recording to one adjacent track.

Furthermore, the track having a specified playback signal quality can be recorded after recording to both adjacent tracks.

Furthermore, the track having a specified playback signal quality can be recorded multiple times.

Further preferably, playback signal quality is the same specified level in all of a specific number of recordings.

The optical disc drive could record at a second emission power level after recording at a first emission power level, the first emission power level being higher than the second emission power level.

An optical disc drive according to the present invention determines the emission power for recording according to the detected playback signal quality.

Further preferably, the emission power is determined in an area outside the user area for recording user data.

With the configuration of an optical storage medium inspection apparatus according to the present invention described above jitter not including jitter relating to marks and spaces of the shortest recordable length is measured and used to determine whether the optical storage medium is good or defective. More specifically, two threshold values are used to identify the shortest marks. When using a two-layer optical storage medium to which data is recorded with the same recording density on two data recording surfaces, this reduces the effect of increased jitter resulting from marks on the recording layer closer to the optical pickup head being smaller than the desired size, and enables a reliable good/defective determination. The effect of degraded jitter resulting from the shortest marks and spaces can likewise be reduced when applied to an optical disc drive, and data can be reproduced with high reliability from two data recording layers. Data can also be recorded and reproduced with high reliability using an optical storage medium on which jitter from the shortest marks and spaces is worse than jitter from longer marks and spaces.

BRIEF DESCRIPTION OF THE DRAWINGS

The objects, features, and benefits of the present invention will be known from the preferred embodiments of the invention described below in conjunction with the accompanying drawings.

DESCRIPTION OF THE PREFERRED EMBODIMENTS

Figure 1:
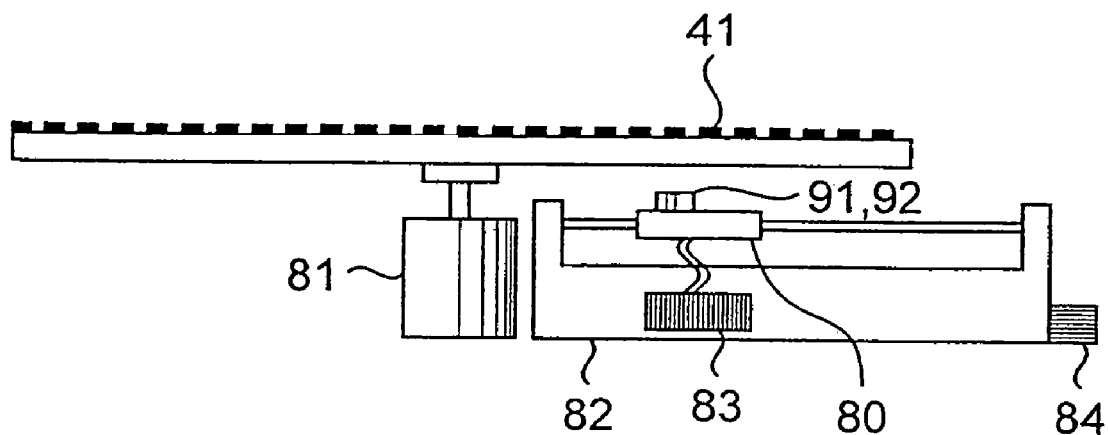
FIG. 1 is a schematic drawing of the configuration of an optical disc drive according to a first embodiment of the present invention.

Preferred embodiments of an optical disc drive according the present invention are described below with reference to the accompanying figures. It should be noted that like reference numerals in the accompanying figures denote identical elements or elements effecting the same action or operation.

Embodiment 1

FIG. 1 shows an example of the configuration of an optical disc drive according to a first embodiment of the present invention. This optical disc drive has an optical pickup head 80, optical disc drive unit 81, optical pickup head drive unit 82, signal processing unit 83, and power supply unit 84. A configuration having a power supply unit 84 is shown in the figure, but a configuration in which a connection terminal (not shown) to an external power supply (not shown) is provided instead of power supply unit 84 and power is supplied by connecting the external power supply and connection terminal could be used. Furthermore, the configuration of the optical pickup head 80 is in no way limited, and the optical pickup head of this embodiment is identical to the conventional configuration shown in FIG. 9.

The function of each of these components is described next. The optical disc drive unit 81 spins the optical disc 41. The optical pickup head 80 sends a signal corresponding to the relative positions of the optical pickup head 80 and optical disc 41 to the signal processing unit 83. The signal processing unit 83 amplifies or operates on the received signal to generate a focus error signal and TE signal, and moves the optical pickup head 80 or objective lens in the optical pickup head as needed. The optical pickup head 80 also sends the read signal of the data recorded to the optical disc 41 to the signal processing unit 83. The signal processing unit 83 demodulates the data recorded to the optical disc 41. Actuators 91, 92 drive the objective lens in the optical pickup head 80.

The optical pickup head drive unit 82 is typically called a traverse mechanism, and positions the optical pickup head 80 so that the beam emitted from the optical pickup head 80 is focused on a desired position on the optical disc 41. The above-noted read signal and optical pickup head drive unit 82 or actuators 91, 92 form a focusing servo and tracking servo for the optical disc 41 to read, write, or erase information. Power is supplied from the power supply unit 84 to the signal processing unit 83, optical pickup head drive unit 82, optical disc drive unit 81, and actuators 91, 92.

It should be noted that a power supply or connection terminal to an external power supply could be disposed to the individual drive circuits.

Figure 7:
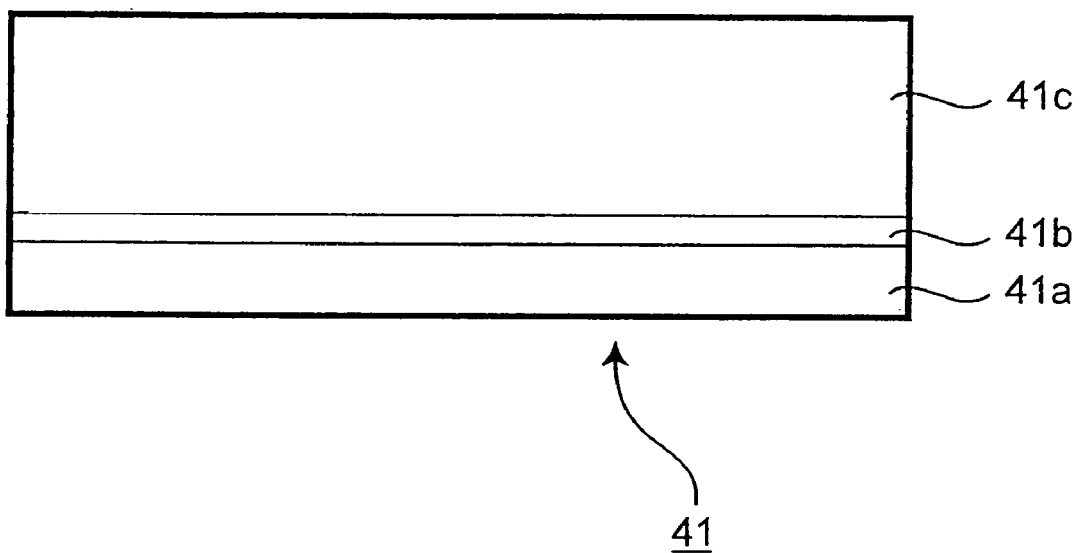
FIG. 7 shows the configuration of an optical storage medium according to a second embodiment of the present invention.

As shown in FIG. 7, the optical disc 41 has two data recording layers 41b, 41c, as does the conventional optical storage medium 40. Data recording layer 41b is semi-transparent. The optical disc 41 of the present embodiment differs from the conventional optical storage medium 40 described above in that whereas the conventional optical storage medium 40 records data using uses 8-16 modulation, that is, a modulation method in which the length of the shortest marks and spaces is 3T, data is recorded to the optical disc 41 of this invention using 1-7 modulation, that is, a modulation technique in which the length of the shortest marks and spaces is 2T and mark length is limited. Modulation using a limited mark length is known as run length limited (RLL) modulation, and in this case is expressed as RLL(1,7) modulation.

Figure 2:
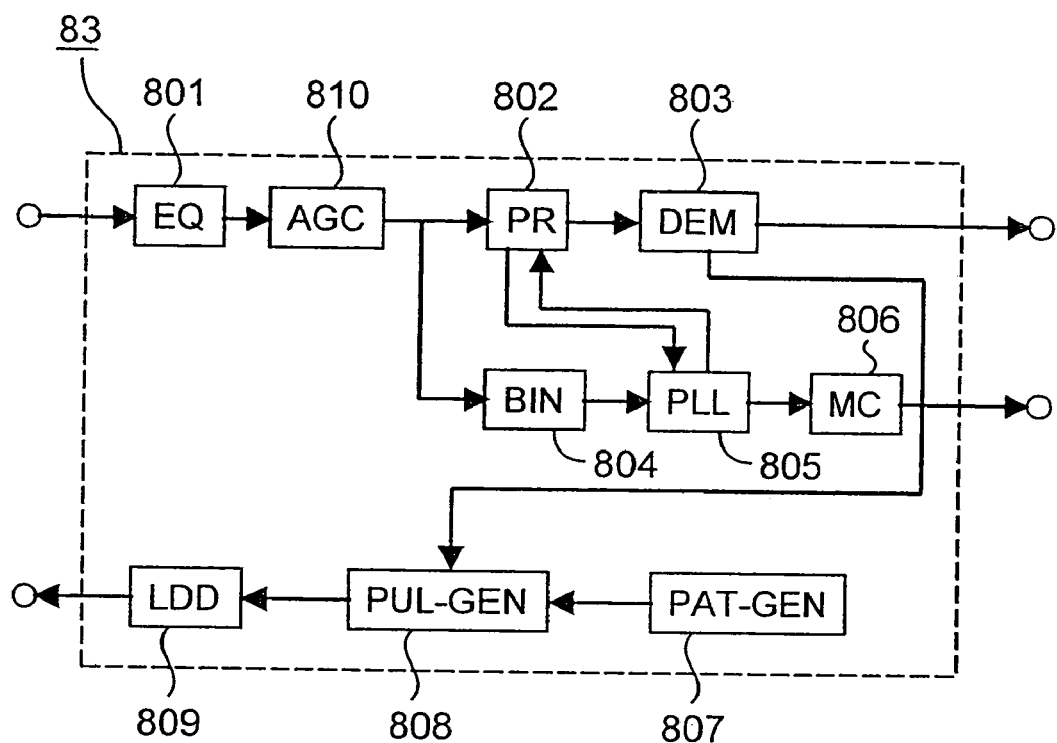
FIG. 2 shows the configuration of the signal processing part of an optical disc drive according to a first embodiment of the present invention.

FIG. 2 is a block diagram of a specific configuration of the signal processing unit 83, showing the configuration of the part for demodulating data and the configuration of the part for generating the recording signal used to record data to the optical storage medium.

The signal output from optical pickup head 80 is input to the equalizer 801. Because the high frequency component is reduced in the signal output from optical pickup head 80 dependent on the optical frequency characteristic, the equalizer 801 enhances the high frequency component of the input signal and thus compensates for the drop in the high frequency range of the optically degraded signal.

The amplification gain of the signal output from the equalizer 801 is automatically adjusted so that the signal amplitude is constant by the automatic gain controller 810. The automatic gain controller 810 can be omitted because the optical disc drive can function without it. However, providing the automatic gain controller 810 reduces the effect of fluctuations in the reflectivity of the optical disc 41, and thereby improves the reliability of the optical disc drive. Furthermore, the automatic gain controller 810 could be located before the equalizer 801. The signal output from the automatic gain controller 810 is input to both digitizer 804 and partial response unit 802.

The digitizer 804 converts the input signal to two values, 0 and 1. The binary signal is then input to clock signal generator 805, and the clock signal generator 805 generates a clock signal with timing set according to the signal recorded to the optical disc 41. The clock signal generator 805 can be configured with a common phase-locked loop (PLL) using a phase comparator, low-pass filter, or VCO, for example. However, the S/N ratio of signals obtained from 2T marks and spaces is often poor when 1-7 modulation is used. When the clock signal is generated using the edges of all marks and spaces, clock signal jitter increases and the data recorded to the optical disc cannot be faithfully reproduced.

When the optical disc drive first starts up the clock signal is generated using all mark and space edges, and after the PLL locks, the results of phase comparison relating to the edges of 2T marks and spaces are eliminated from the phase comparator output used to generate the clock signal. The partial response unit 802 identifies the 2T marks and spaces, and the result of this 2T mark and space identification is sent from the partial response unit 802 to the clock signal generator 805. The PLL is locked more easily when the optical disc drive first starts up by using all mark and space edges. Furthermore, clock signal jitter can be reduced by eliminating the results of phase comparison relating to the edges of 2T marks and spaces once the PLL is locked. As a result, the clock signal generator 805 of an optical disc drive according to this embodiment of the invention can output a low-jitter clock signal even when the recording density of the optical storage medium is increased and the SNR of signals obtained from 2T marks and spaces is low, and data can be reproduced with a corresponding increase in reliability.

The clock signal generated by the clock signal generator 805 is input to the optical disc drive signal generator 806 and partial response unit 802. The optical disc drive signal generator 806 generates an optical disc drive signal controlling the drive speed of the optical disc 41 according to the input signal. The optical disc drive signal generated by the optical disc drive signal generator 806 is then supplied to the optical disc drive unit 81. The signal output from the partial response unit 802 is input to demodulator 803 whereby the signal recorded to the optical disc 41 is demodulated.

Figure 3:
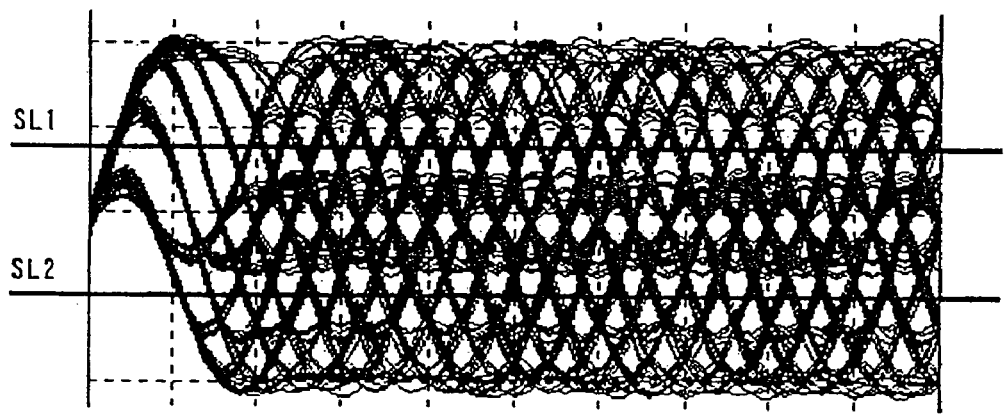
FIG. 3 shows an RF signal obtained by an optical disc drive according to a first embodiment of the present invention.

FIG. 3 shows the relationship between the threshold values (SL1, SL2) set by the partial response and the eye pattern. A first threshold value SL1 is set between the signal obtained from a 2T mark and the signal obtained from a 3T mark, and a second threshold value SL2 is set between the signal obtained from a 2T space and the signal obtained from a 3T space. The partial response unit 802 samples signals output from the automatic gain controller 810 at the clock signal edge and identifies the length of the marks and spaces. By setting this first threshold value SL1 and second threshold value SL2, 2T marks and spaces can be identified with good precision when the 2T signal amplitude is low. Furthermore, by also using maximum likelihood decoding such as the Viterbi algorithm, that is, by using PRML (Partial Response Maximum Likelihood) decoding, 2T marks and spaces can be accurately identified even when the signal amplitude obtained from the 2T marks and spaces is low when a different class such as (1,2,2,1) is used in the partial response unit.

Figure 4:
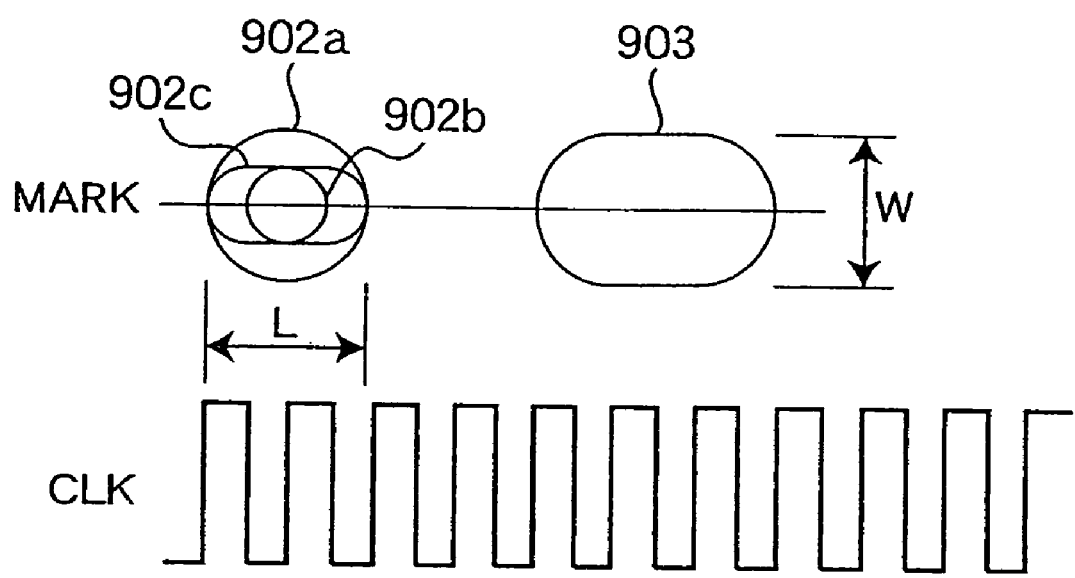
FIG. 4 shows the relationship between a clock signal and marks on an optical storage medium in an optical disc drive according to a first embodiment of the present invention.

FIG. 4 shows the relationship between the clock signal CLK generated by the clock signal generator 805, and marks recorded to data recording layers 41b, 41c of the optical disc 41. Marks 902a to 902c are 2T marks and mark 903 is a 3T mark where a 2T mark is 0.15 µm long and a 3T mark is 0.225 µm long. The 2T and 3T marks recorded to data recording layer 41c are marks 902a and 903, respectively, each having the same mark width W. The 2T and 3T marks recorded to data recording layer 41b are marks 902b and 903, mark 902b being smaller in both width W and length L than mark 902a. Mark 902b can be formed similarly to mark 902c by changing the mark recording conditions. The length L of mark 902b can be increased at this time, but the width W necessarily remains smaller than mark 902a. This can be summarized as follows.

First, when a mark of length 2T is formed in data recording layer 41c, it can be formed to the same width as a mark of length 3T. However, when a 2T mark is recorded to data recording layer 41b, it cannot be formed with sufficient width compared with a 3T mark. This is because the semi-transparent nature of the data recording layer 41b increases the heat dissipation time of the data recording layer 41b, and a type of erasing action works on the recorded mark.

This phenomenon occurs not only with phase-change materials, but also with magneto-optical materials and any other type of material that uses heat to record or erase data. It should be noted that 4T and longer marks have the same width as 3T marks. The decrease in mark size becomes more pronounced as mark length decreases, and usually cannot be ignored at $I/(NA*2.5)$ or less. More specifically, if NA is 0.85 and I is 0.405 µm, this effect cannot be ignored when mark length is 0.190 µm or less. Under conditions in which the mark size decreases the aperture ratio of the eye of the eye pattern decreases, and jitter increases after binarization as a result. This means that there is a relative increase in jitter when the length of the shortest marks and spaces is 2T compared with longer marks and spaces with a length of 3T or greater.

Because the 2T mark length is 0.15 µm and the 3T mark length is 0.225 µm in the present embodiment, 2T marks are narrower in width than the other longer marks, and there is a dramatic increase in jitter after binarization. To address this problem, this embodiment of the invention sets two threshold values and detects signals with a partial response. Even if the width of a 2T mark is narrow, it will not produce an RF signal exceeding both threshold values and will not adversely affect data detection. In other words, even if 2T marks are recorded to the data recording layer 40b with a narrow width, the data can still be reproduced with high reliability.

Figure 5:
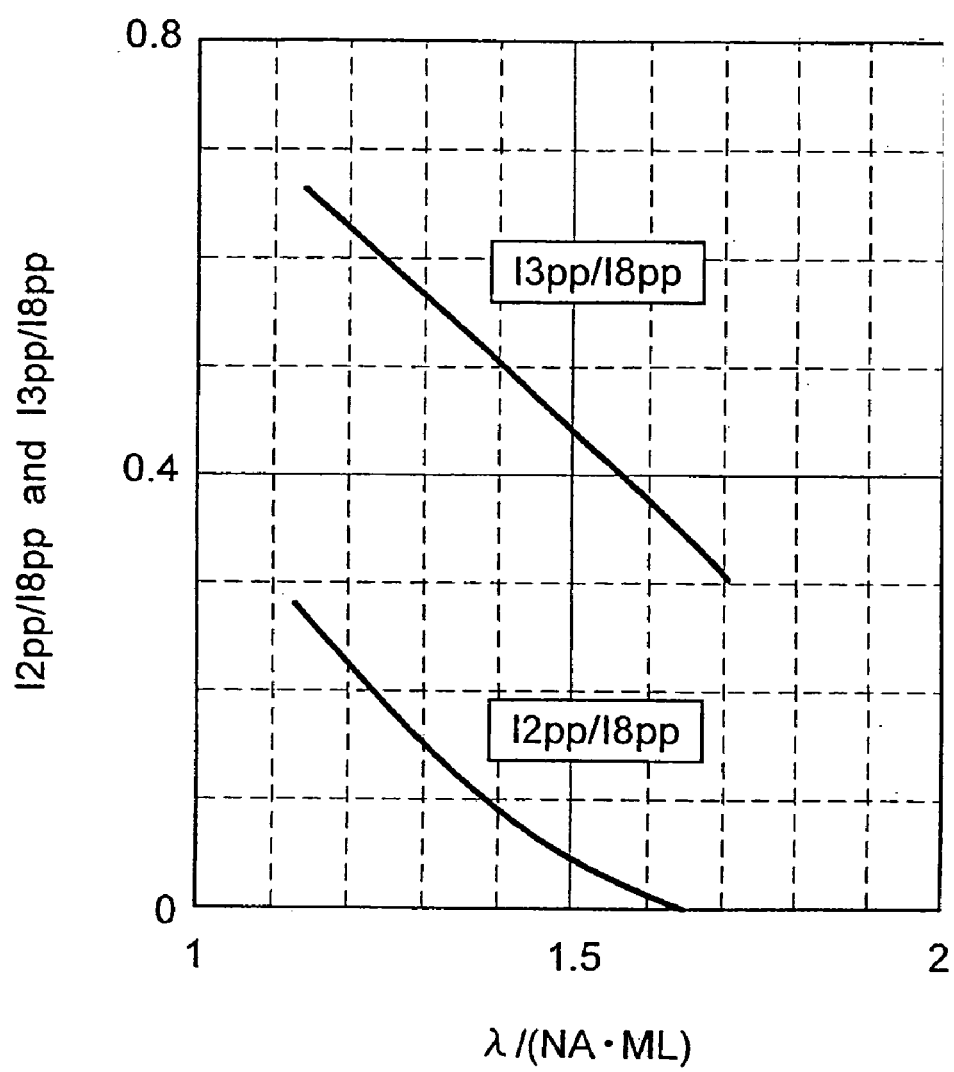
FIG. 5 shows the relationship between signal amplitude and mark length on an optical storage medium in an optical disc drive according to a first embodiment of the present invention.

FIG. 5 shows the relationship between mark length and signal amplitude. The horizontal axis in FIG. 5 represents $\lambda/(ML*NA)$ where $\lambda$ is the wavelength of the light source, NA is the numeric aperture of the objective lens in the optical pickup head, and ML is the length of a pair of marks and spaces of equal length. On the vertical axis 12 pp/18 pp is the signal amplitude from a pair of 2T marks and spaces divided by the signal amplitude from a pair of 8T marks and spaces. Likewise, 13 pp/18 pp is the signal amplitude from a pair of 3T marks and spaces divided by the signal amplitude from a pair of 8T marks and spaces.

What is known from FIG. 5 is described next. When $I/(ML*NA)$ is approximately 1.25, 12 pp/18 pp is 0.2 and 13 pp/18 pp is 0.6, and the ratio between 12 pp and 13 pp is therefore 1:3. If the 2T mark width is narrower than the 3T mark width, this ratio is even greater. When $I/(ML*NA)$ is greater than 1.25, 12 pp/18 pp drops rapidly and the amount of noise from the optical storage medium, laser, circuits, and other factors relative to 12 pp increases relatively sharply in conjunction with the drop in 12 pp/18 pp. As a result, jitter increases at the edges of 2T marks and spaces with conventional methods that simply detect a binary signal.

The gap between the threshold value and signals obtained from 2T and 3T marks or spaces increases when two threshold values are used, i.e., it is easier to detect the difference between 2T long marks and spaces and 3T long marks and spaces. Therefore, when ML is the length of a pair of 2T marks and spaces and $I/(ML*NA)$ is greater than 1.25, it is effective to use PRML detection and a partial response unit using two threshold values.

It should be noted that an optical disc 41 having two recording layers is described here, but the invention shall not be so limited. For example, when the characteristics of the recording layers of the optical storage medium result in 2T marks that are narrower than 3T and longer marks, and when $I/(ML*NA)$ is greater than 1.25 when ML is the length of a pair of 2T marks and spaces, it will be obvious that an optical disc drive according to the present invention can reproduce data with high reliability regardless of the number of recording layers.

Furthermore, the optical disc drive of this invention is not limited to reading and writing optical storage media that can be recorded any number of times, and can be used with write-once read-many optical storage media and with read-only optical storage media.

For example, when the mother disc is cut using a laser beam in the mastering process for producing a read-only optical storage medium, the width of 2T marks could become narrower than the width of 3T and longer marks. Considering that shortest wavelength of the laser beam that can be used for cutting the mother disc is approximately 270 nm and the maximum numeric aperture of the objective lens is approximately 0.9, the width of 2T marks is unavoidably narrower than the width of 3T and longer marks when producing a high density read-only optical storage medium with a 0.4 µm or smaller track pitch and a shortest mark length of 0.2 µm. The effect of an optical disc drive according to this embodiment of the invention is particularly great in this case.

Another method is to use a nonlinear transparent film for the resist film to form small marks when cutting the mother disc using a laser beam, but the width of 2T marks is also often narrower than the width of 3T and longer marks in this case. An optical disc drive according to this embodiment of the invention is also extremely effective in this case.

When an electron beam is used to cut the mother disc 2T marks and 3T marks can be formed with the same width, but because the cutting time is significantly greater than when a laser beam is used, the cost of the optical storage media is accordingly higher. Using an optical disc drive according to this embodiment of the invention therefore enables cutting the mother disc using a laser beam and thus provide a low-cost optical storage medium.

The shortest marks are also not limited to a 2T mark length, the benefit of the present invention can be achieved when the width of the shortest mark is narrower than the width of marks longer than the shortest mark, and the length of the shortest mark could be 3T, for example.

It will be further noted that while a conventional optical pickup head is used in the preceding embodiment, any type of optical pickup head that emits a beam to the optical storage medium and outputs a signal based on the beam reflection from the optical storage medium could be used. In addition, a clock signal is generated using an RF signal recorded to the optical storage medium, but any conventional method of generating a clock signal could be used, including methods for generating the clock signal from the timing of the wobble in a wobble groove used as the track.

The system for recording data is described next.

(a) The digital pattern generator 807 converts the audio, video, computer data, or other information to a desired digital data pattern based on the modulation rules for 1-7 modulation. The digital pattern generator 807 also has a function for generating a simple pattern, random pattern, and special pattern comprising a combination of specific mark and space lengths in order to learn the optimum recording conditions for the optical storage medium.

(b) The digital data pattern generated by the digital pattern generator 807 is then input to the recording pulse generator 808.

(c) Based on the input digital data pattern, the recording pulse generator 808 generates a recording pulse signal for recording marks and spaces to the optical storage medium. The recording pulse signal can adjust width, amplitude, and timing. The recording pulse generator 808 also has memory for storing information specific to the optical storage medium, the learned optimal results, the recording conditions recorded to the optical storage medium, and other information. This makes it possible to shorten the time needed to learn recording conditions when recording to a disc for which learning was previously completed, or to a disc to which the optimal recording conditions have already been recorded.

(d) The recording pulse signal generated by the recording pulse generator 808 is then input to laser drive device 809.

(e) The laser drive device 809 then controls the output of the semiconductor laser that is the light source of the optical pickup head based on the supplied recording pulse signal to record data to the recording layer of the optical disc.

Figure 6:
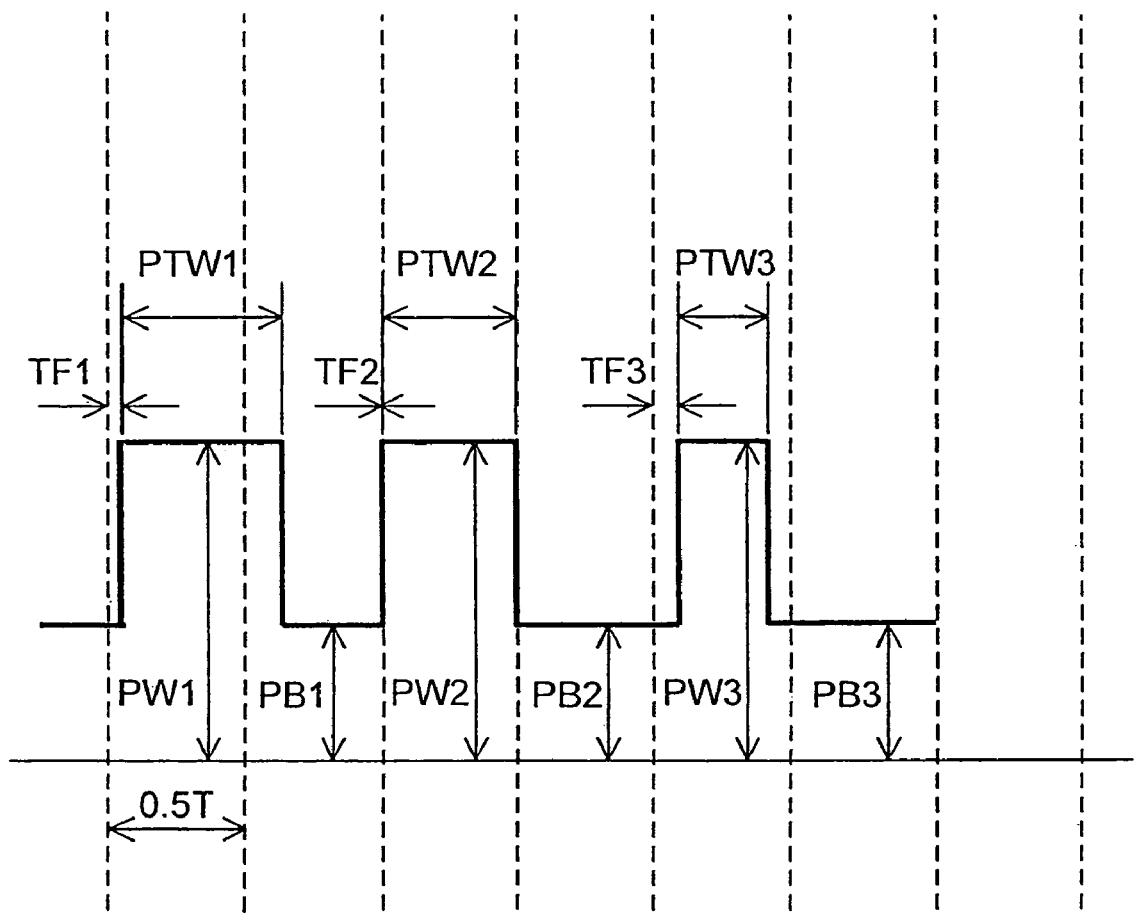
FIG. 6 shows recording pulses in an optical disc drive according to a first embodiment of the present invention.

FIG. 6 shows the recording pulse signal for recording 3T marks. The pulse count increases according to the mark length such that the pulse count for a 3T mark is three and the pulse count for a 5T mark is five. The dotted lines denote the timing of the clock signal edges. PTW1, PTW2, and PTW3 denote the recording pulse width, TF1, TF2, and TF3 denote the delay time from the clock signal edge timing to the rising edge of the recording pulse, PW1, PW2, and PW3 denote the peak power of the recording pulse, and PB1, PB2, and PB3 denote the bias power.

These values are optimized according to the characteristics of the optical storage medium, the length of the recorded mark, and the length of the spaces before and after the recorded mark. PW1 to PW3 could therefore be different values. The same is true for PTW1 to PTW3 and PB1 to PB3. Depending upon the characteristics of the laser drive device 809, the recording conditions could be optimized by adjusting PTW1 to PTW3 while PW1 to PW3 and PB1 to PB3 are set to the same values, or by optimizing PW1 to PW3 and PB1 to PB3 while holding PTW1 to PTW3 constant.

The optimum power, amplitude, and delay time are likewise set for marks and spaces of other lengths. Furthermore, the delay time could be positive or negative depending on the optical storage medium characteristics. To learn the recording conditions a 1-7 modulation random signal is recorded to the optical disc and the recording pulses are adjusted so that the average of the time period of signals obtained from 2T to 8T marks and spaces are equal at an integer multiple of the respective T. This enables the average of 2T marks and spaces to be matched to the threshold values set for digitizing signals obtained from 3T and longer marks and spaces. By matching the average of 2T marks and spaces with the threshold values set for digitizing signals obtained from 3T and longer marks and spaces, the highest likelihood of creating an error is reduced when data is reproduced using two threshold values and a high reliability optical disc drive can be provided.

Recording pulses can also be optimized for 3T or longer marks and spaces not adjacent to 2T marks or spaces using jitter or the error rate as the evaluation function. The likelihood of errors can be reduced more in this case than when optimization is based solely on the time period of the signals obtained from the marks and spaces, and reliability can be further improved. The recording conditions can be optimized in which case by recording without using 2T marks and spaces. This also eliminates the need to identify 2T edges, and the recording conditions can therefore be learned more easily and in less time.

Furthermore, if jitter not including signals relating to edges adjacent to 2T marks and spaces exceeds a desired level when data is recorded after optimizing recording conditions in an allowable range, the optical storage medium is determined unsuitable for recording data and the data that would otherwise be recorded to the optical storage medium is not recorded. A report that the optical storage medium is not suitable for recording data could also be output. This assures that when important information is recorded to the optical storage medium, the information can be reproduced with high reliability.

Recording conditions have conventionally been evaluated using the jitter produced from the edges of all marks and spaces. It is not possible with this method, however, to determine whether jitter is bad at the edges adjacent to 2T marks and spaces. That is, it is not possible to differentiate between when jitter from the edges not adjacent to 2T marks and spaces is significantly lower than jitter from the edges adjacent to 2T marks and spaces, and when jitter for edges not adjacent to 2T marks and spaces is the same as jitter from edges adjacent to 2T marks and spaces. Whether an optical disc is suitable for recording information has therefore been determined based simply on whether jitter detected from all edges is greater than or less than a desired threshold value. In this case, however, the error rate when data is reproduced using PRML can differ greatly even for optical discs that have the same apparent jitter level. In order to record and reproduce data reliably it has therefore been necessary to identify media having a certifiably low error rate by using a low jitter threshold value, and even media that have a sufficiently low error rate when PRML methods are used must be treated as optical disc media that is unsuitable for recording information.

With the optical disc drive according to this embodiment of the invention, however, jitter not including results for edges adjacent to 2T marks and spaces is used as the evaluation function, and there is an extremely strong correlation between this jitter value and the error rate when PRML is used. The jitter level can therefore be set higher than is conventionally used, and optical storage media with which a low error rate is obtained when PRML is used can be reliably identified. Optical storage media production yield can therefore be improved, and low cost optical storage media can be provided. It will be obvious that this optical storage medium is not limited to using PRML, and can be achieved using other two-threshold-value partial response detection methods. While 1000 to 10,000 edges are needed when jitter is used as the evaluation function, 100,000 to 1,000,000 edges are needed when the error rate is used as the evaluation function. When jitter is used as the evaluation function the time required for media evaluation is significantly shorter than when the error rate is used as the evaluation function, and optical storage media productivity can therefore be improved.

Embodiment 2

The configuration of an optical storage medium according to another embodiment of the present invention is shown in FIG. 7. This optical disc 41 has a transparent protective layer 41a and two recording layers 41b, 41c. This optical disc 41 differs from optical storage medium 40 in that data recording layer 41c is a recording layer that can be rewritten multiple times, and data recording layer 41b is a read-only recording layer. Marks are formed in data recording layer 41b by embossing. The shortest marks and spaces are also 2T. The transmittance of data recording layer 41b is also greater than 50%, and in this preferred embodiment is 80%. Because it is read-only, the transmittance of data recording layer 41b is substantially constant throughout the entire layer. Furthermore, because data recording layer 41b, which is a read-only recording layer, is on the light incidence side of data recording layer 41c, the power of the beam emitted to data recording layer 41c is stable because the transmittance of data recording layer 41b is constant, and the desired information can be written and read.

Furthermore, because data recording layer 41b is read-only, the transmittance of data recording layer 41b can be set higher than 50%. The emission power of the laser part of the optical pickup head required to record to the data recording layer 41c is therefore lower, the service life of the laser is therefore longer, and an optical disc drive that can be used for a longer period of time can therefore be provided.

Furthermore, because the beam strength incident on the receptor when reading data recorded to data recording layer 41c is increased by the higher transmittance of data recording layer 41b, the SNR is also improved and data can be reproduced with high reliability.

It should be noted that data recording layer 41c is described above as a rewritable recording layer, but it could alternatively be a write-once recording layer.

Furthermore, if there are three or more recording layers with only one layer being writable and the other layers being read-only data layers, the same effect described above can be achieved by disposing the read-only recording layers on the side of the disc to which the beam from the optical pickup head is incident and disposing the recordable recording layer on the side farthest from the side to which the beam from the optical pickup head is incident.

It should be noted that optical storage media according to this embodiment of the invention shall not be limited to any particular modulation method, and any modulation method can be used.

Embodiment 3

Figure 8:
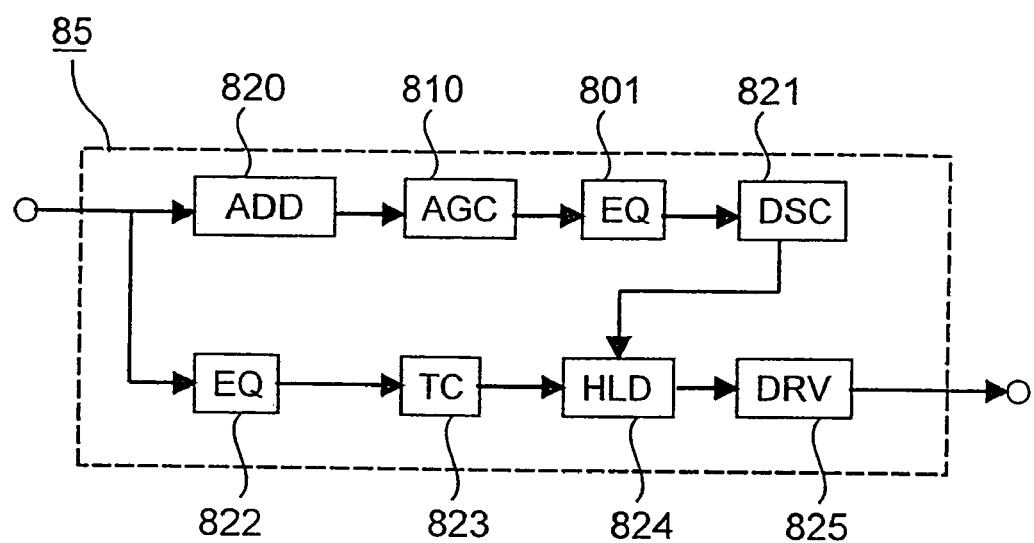
FIG. 8 shows the configuration of the signal processing part of an optical disc drive according to a third embodiment of the present invention.

As another example of an optical disc drive according to the present invention, FIG. 8 shows the configuration of an optical disc drive that generates a TE signal using a phase difference method (also known as a DPD (differential phase detection) method) from an optical storage medium on which 2T marks and spaces are formed as the shortest marks and spaces.

Figure 9:
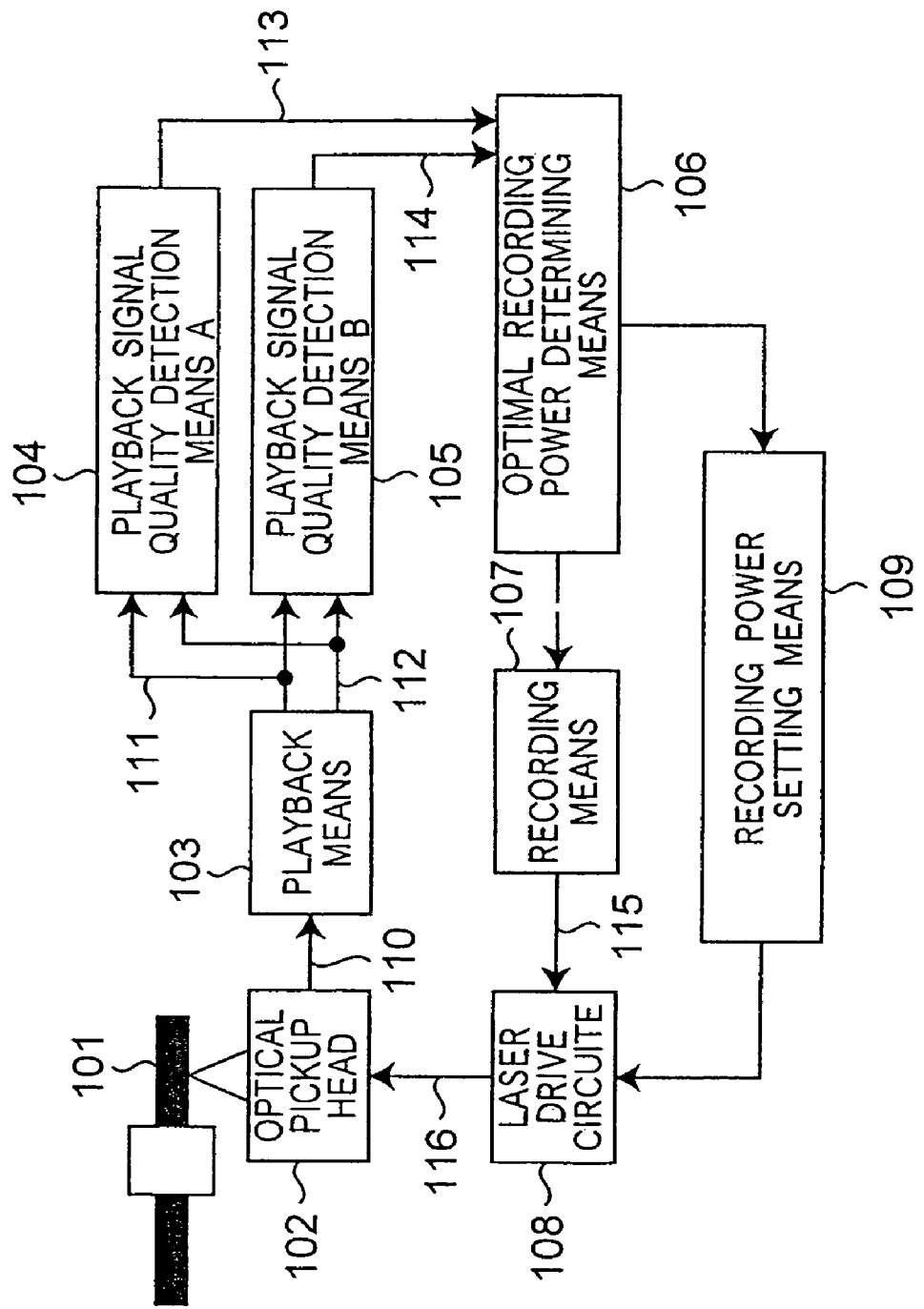
FIG. 9 is a block diagram of an optical disc drive according to a fourth embodiment of the present invention.

An optical storage medium having a recording layer on which embossed marks are formed as described with optical disc 41 according to the second embodiment can be used as the optical storage medium in this embodiment. The optical disc drive can use any type of optical pickup head insofar as the optical pickup head splits the beam in the far field region, detects the reflections with a photodetector, and can output signals enabling phase comparison. This embodiment is described using most common optical pickup head as shown in FIG. 9.

Figure 22:
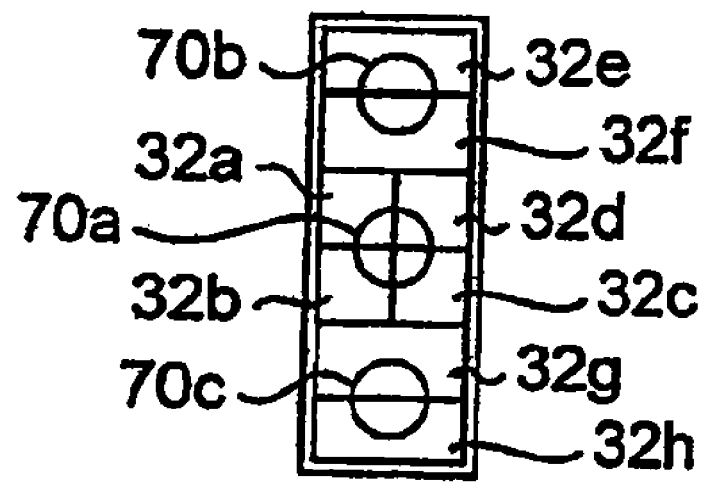
FIG. 22 shows the relationship between the beam and photodetector of the optical pickup head in a conventional optical disc drive.
Figure 23:
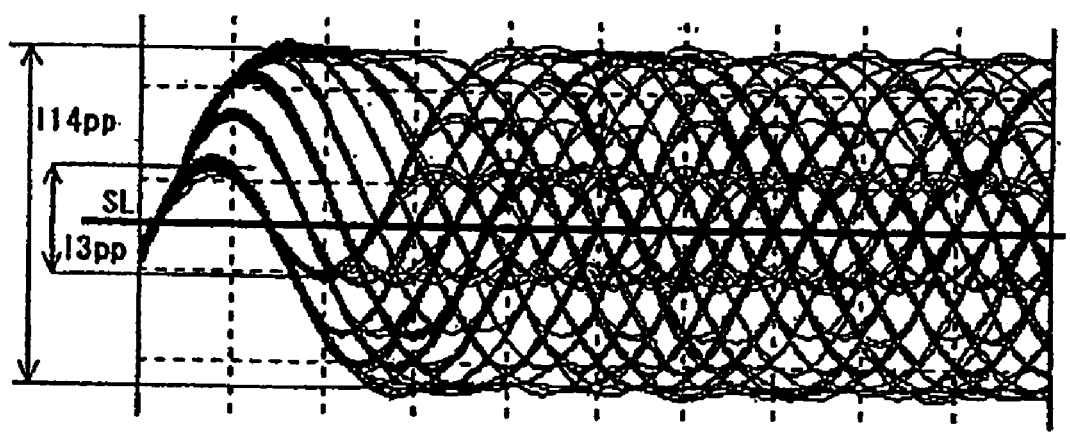
FIG. 23 shows an RF signal obtained by a conventional optical disc drive.
Figure 24:
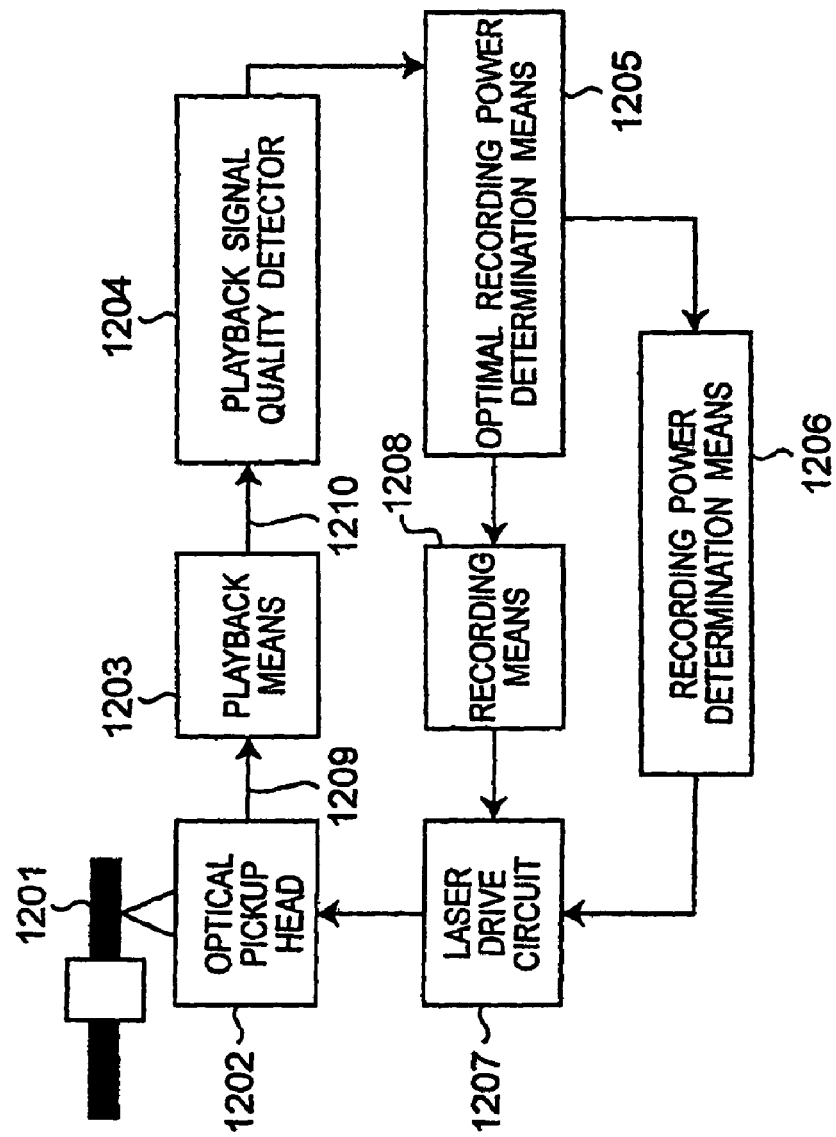
FIG. 24 is a block diagram of a conventional optical disc drive.
Figure 25:
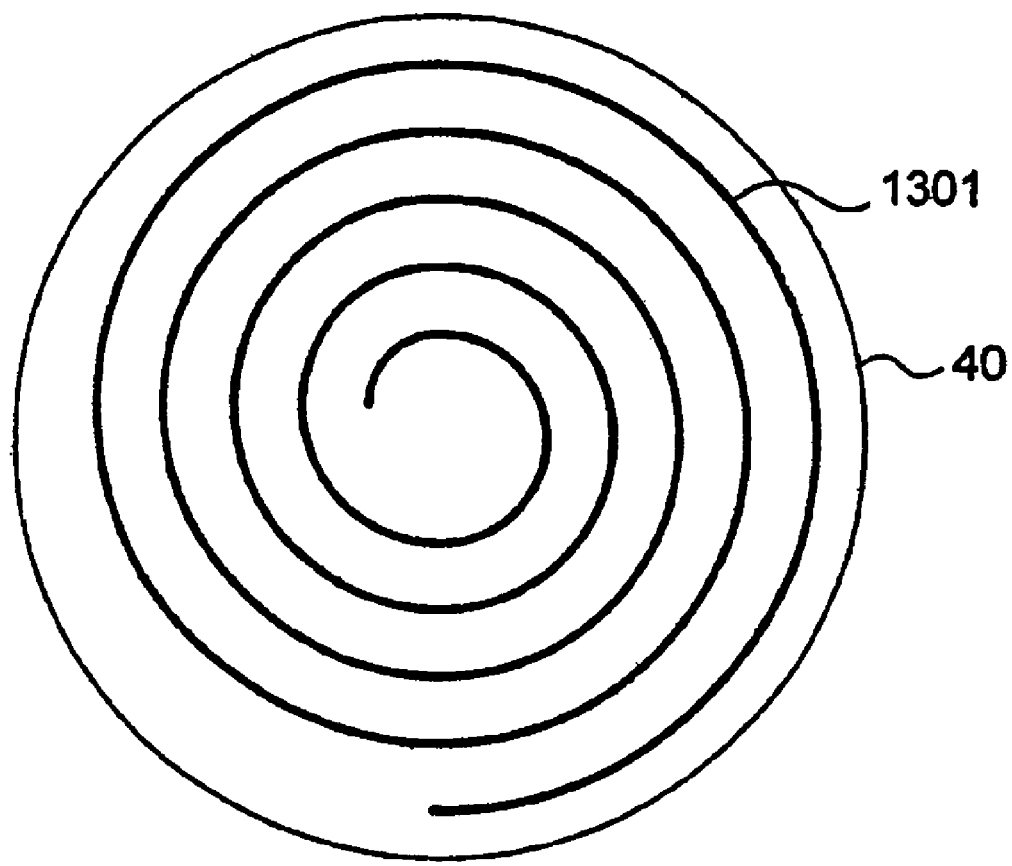
FIG. 25 shows the track configuration of a conventional optical storage medium.
Figure 26:
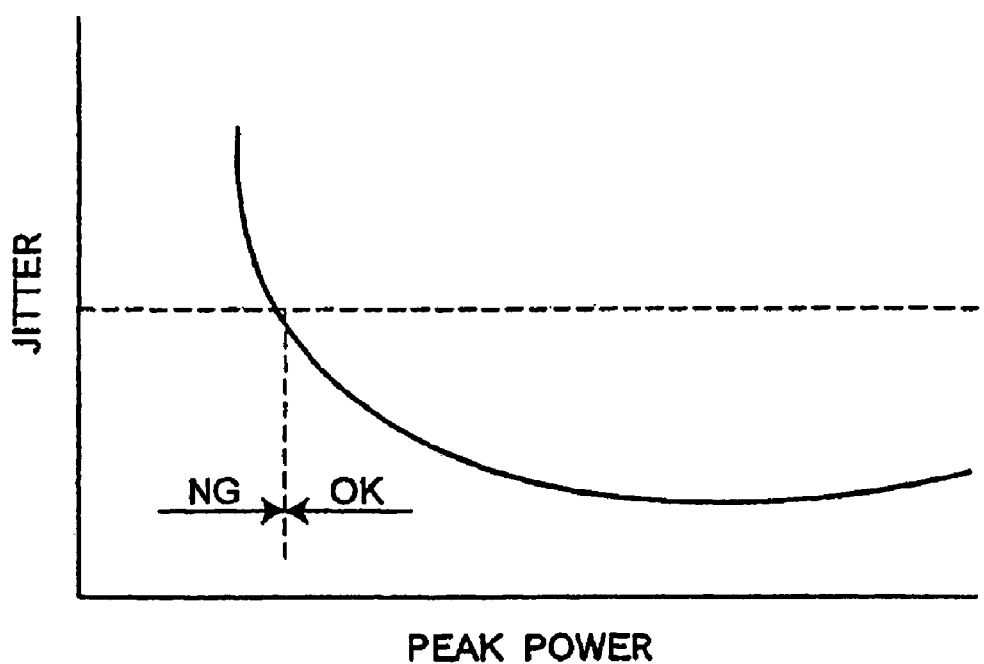
FIG. 26 shows the relationship between peak power and jitter in a conventional optical disc drive.
Figure 27:
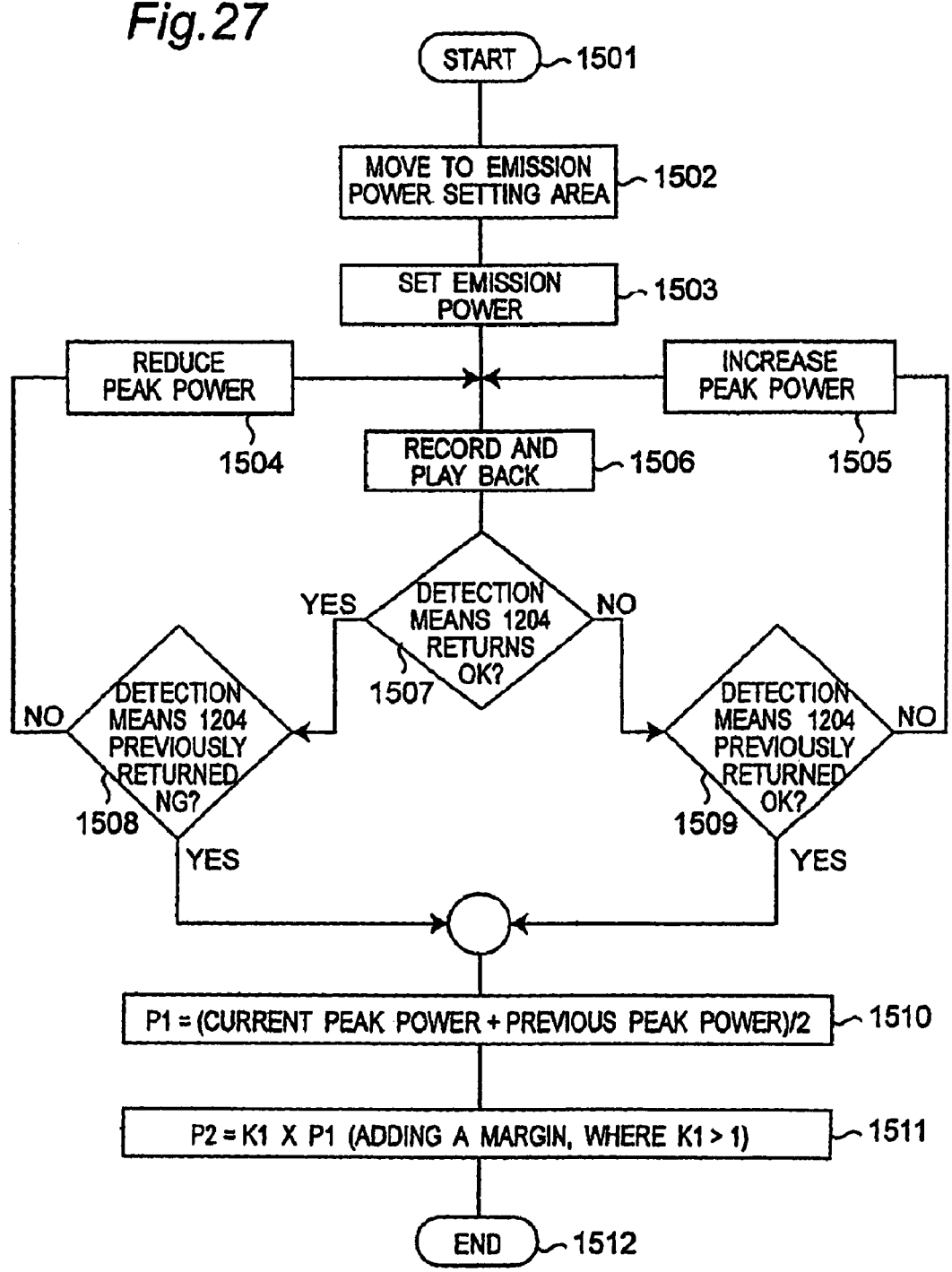
FIG. 27 is a flow chart relating to a conventional optical disc drive.

(a) Signals output from receptors 32a to 32d (see FIG. 22) of photodetector 32 are input to signal processing unit 85.

(b) The signals output from receptors 32a to 32d and input to signal processing unit 85 are added by adder 820 and input to automatic gain controller 810.

(c) The automatic gain controller 810 automatically adjusts the gain so that the input signal amplitude is amplified to a desired level.

(d) The signal output from automatic gain controller 810 is input to equalizer 801 whereby the high frequency component of the signal is emphasized, and the signal is then input to discriminator 821.

(e) The discriminator 821 generates and outputs a hold signal at the edge timing of 2T marks and spaces in the input signal.

(f) Each of the signals output from receptors 32a to 32d is input to equalizer 822 whereby the high frequency components are emphasized and the four signals are then input to phase comparator 823.

(g) The phase comparator 823 outputs a signal denoting the timing at which the amplitude of the input signal changes.

(h) The signal output from phase comparator 823 passes holding circuit 824 and is then input to drive signal generator 825.

(i) The holding circuit 824 considers signals timed to the edges of 2T marks and spaces to be invalid, and therefore does not output to the drive signal generator 825.

(j) The drive signal generator 825 amplifies the input signal to the desired level, applies such processes as phase compensation and bandwidth limiting, and then outputs a signal used to control the tracking control actuator.

When 1-7 modulation is used the SNR of signals obtained from 2T marks and spaces is often worse than signals obtained from marks and spaces longer than 2T. When the TE signal is generated using edges from all marks and spaces, the edge timing detection for 2T marks and spaces is extremely poor, thus significantly degrading the SNR of the TE signal and thus lowering tracking control precision accordingly. By generating the TE signal without using the phase comparison results relating to 2T mark and space edges, the number of edges detected per unit time decreases and it may not be possible to raise the tracking control band. There is, however, a significant improvement in the SNR, and the tracking control band can be raised compared with generating the TE signal using the edge timing for all marks and spaces.

Furthermore, the effect of using the TE signal generating method of this embodiment is particularly great when $I/(ML*NA)$ is greater than 1.25 as when the clock signal is generated as described in the first embodiment.

It should be noted that components not shown in FIG. 8 can use the same configuration used in a conventional optical disc drive, and further description thereof is thus omitted here.

Furthermore, the present embodiment shall not be limited to recording methods in which the shortest mark is 2T long. More specifically, this embodiment can be used when the width of the shortest mark is narrower than the width of marks longer than the shortest mark, and the shortest marks could, therefore, be 3T, for example.

Embodiment 4

FIG. 9 shows the configuration of a phase-change optical disc drive as an example of another optical disc drive according to the present invention. This optical disc drive has an optical pickup head 102, playback means 103, playback signal quality detection means A 104 and detection means B 105, optimal recording power determining means 106, recording means 107, laser drive circuit 108, and recording power setting means 109.

The optical pickup head 102 emits a light beam to the optical disc 101 and receives the reflected light. The playback means 103 reproduces a signal based on the light detected by the optical pickup head 102. Playback signal quality detection means A 104 and detection means B 105 detect the quality of the playback signal. The optimal recording power determining means 106 determines the optimal recording power based on the playback signal quality detected by playback signal quality detection means A 104 and detection means B 105. The laser drive circuit 108 emits a laser beam. The recording power setting means 109 sets the beam power used for recording.

Figure 10:
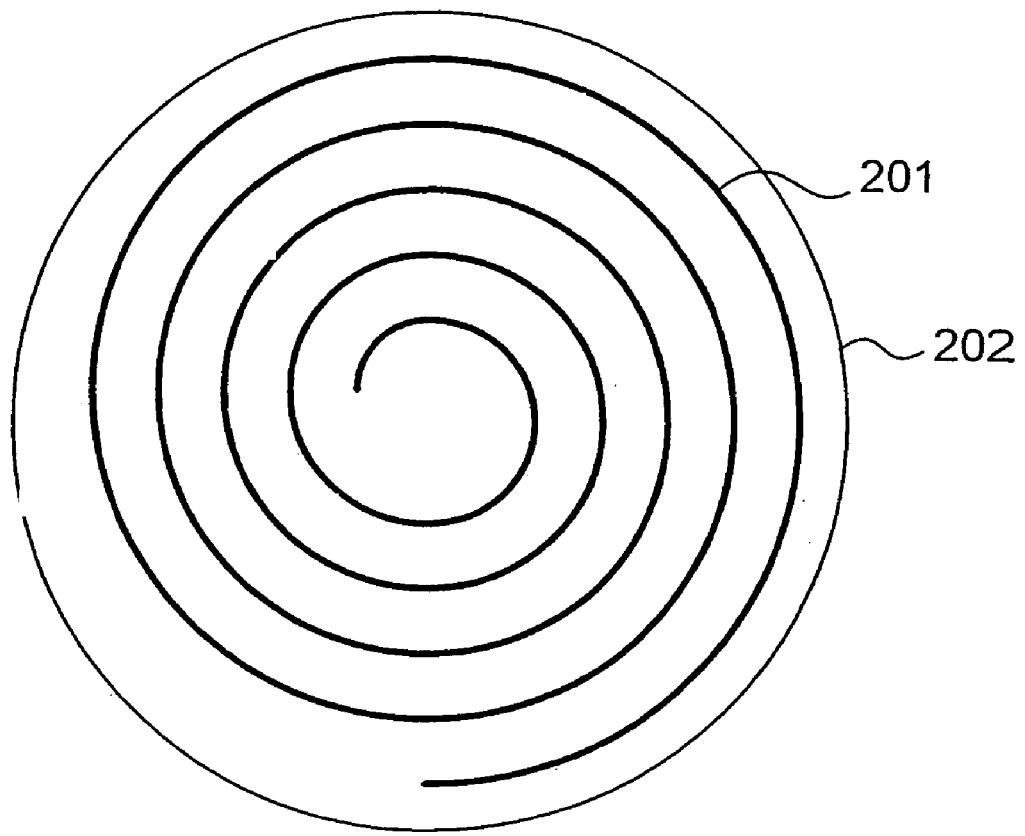
FIG. 10 shows the track configuration of an optical storage medium in a fourth embodiment of the present invention.

FIG. 10 shows the track configuration of the optical disc 101 in this embodiment of the invention. This optical disc 101 is an optical storage medium having a recording area in groove track 201, the groove track being formed in a continuous spiral.

Figure 12:
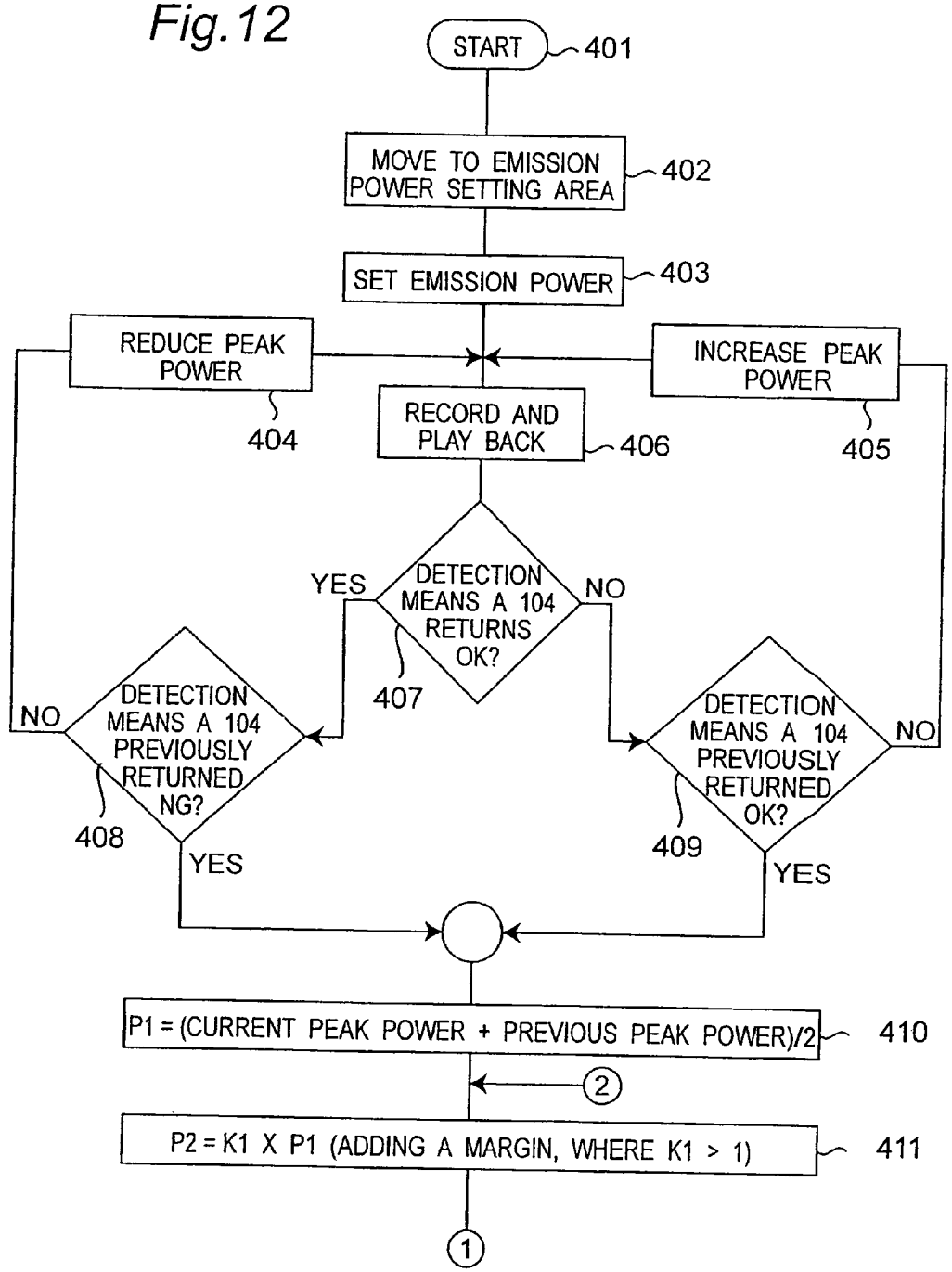
FIG. 12 is a flow chart related to a fourth embodiment of the present invention.

After the optical disc 101 is loaded in the optical disc drive and specific operations such as identifying the optical disc type and rotational control are completed, the optical pickup head 102 moves to an area for setting the optimal recording power (step 402, FIG. 12).

This area is a recording area at the inside or outside circumference of the disc outside of the user area where user data is recorded. Heat damage to the user area from recording at a high output power level is prevented by using an area outside the user area.

Figure 18:
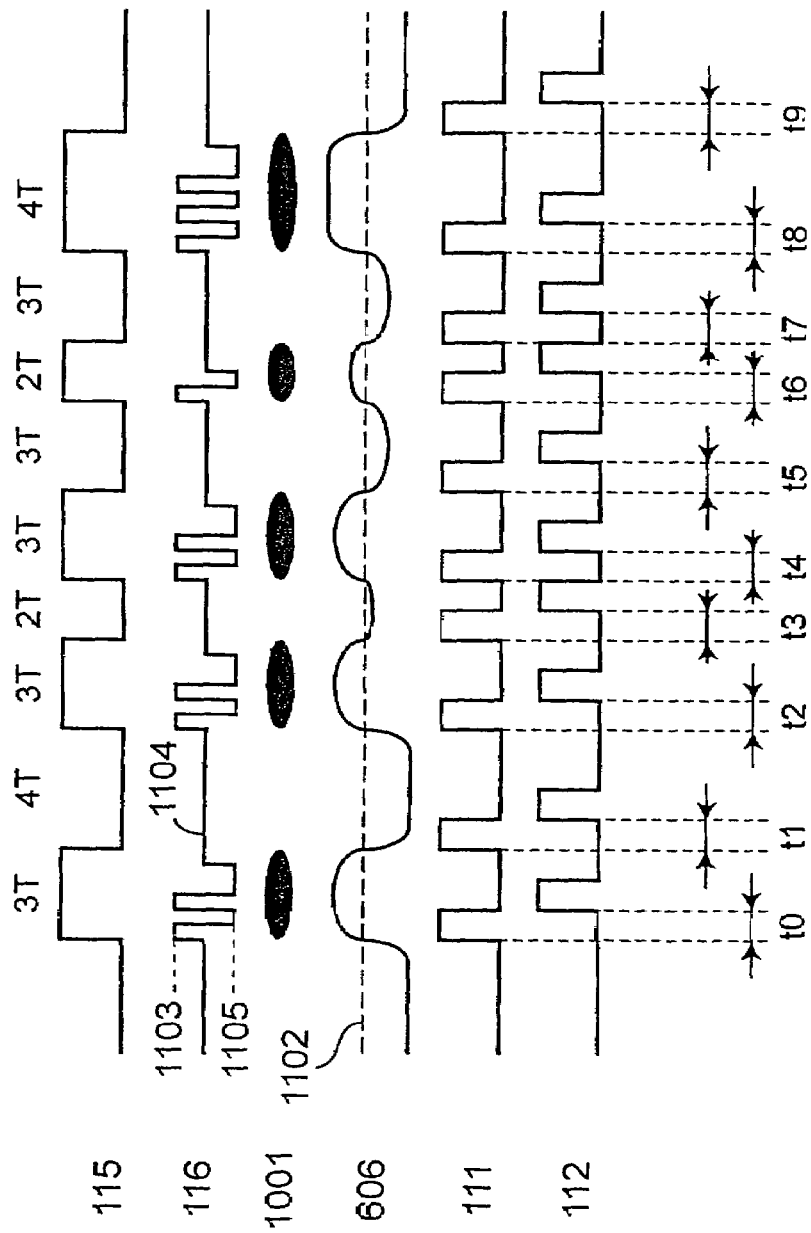
FIG. 18 describes the output signal of an optical disc drive according to a fourth embodiment of the present invention.
Figure 19:
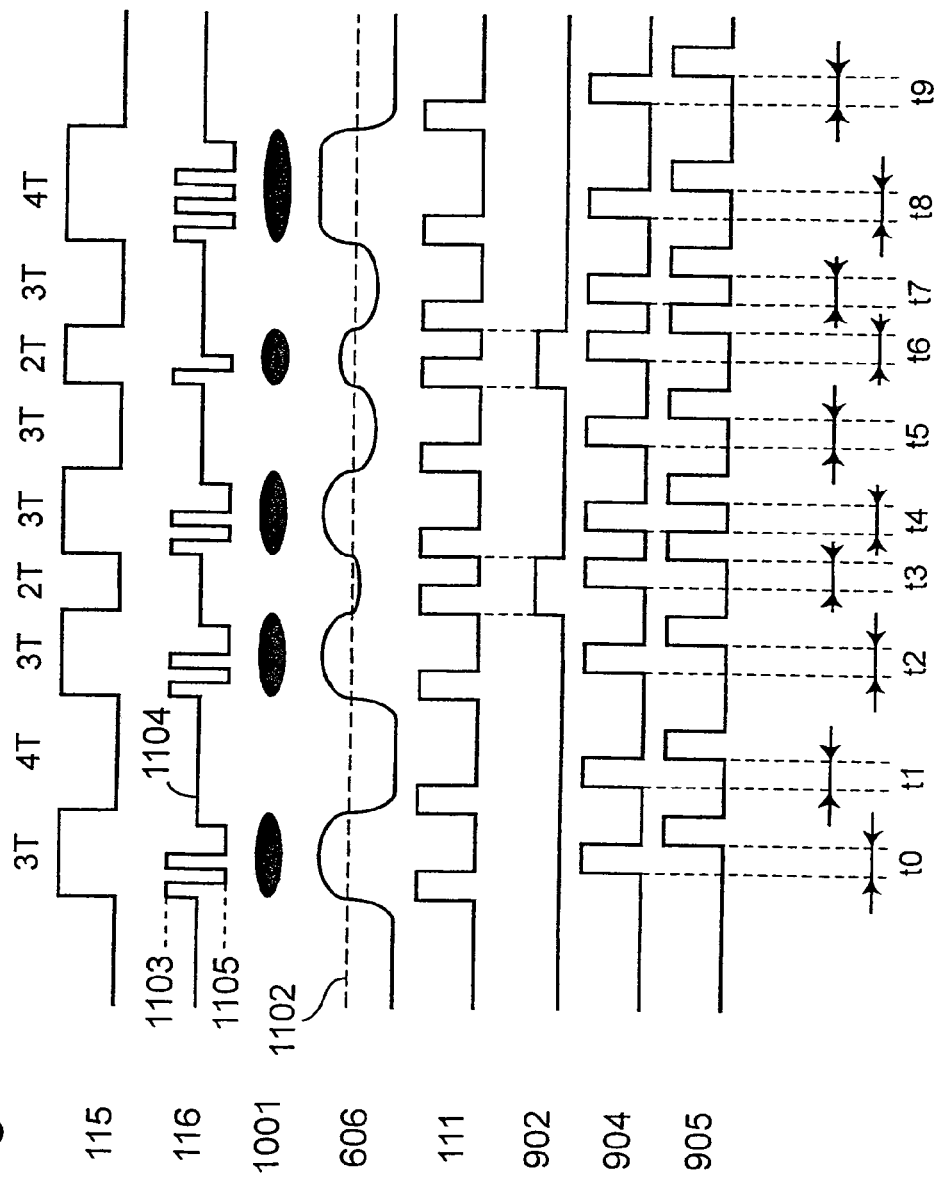
FIG. 19 describes the output signal of an optical disc drive according to a fourth embodiment of the present invention.
Figure 20:
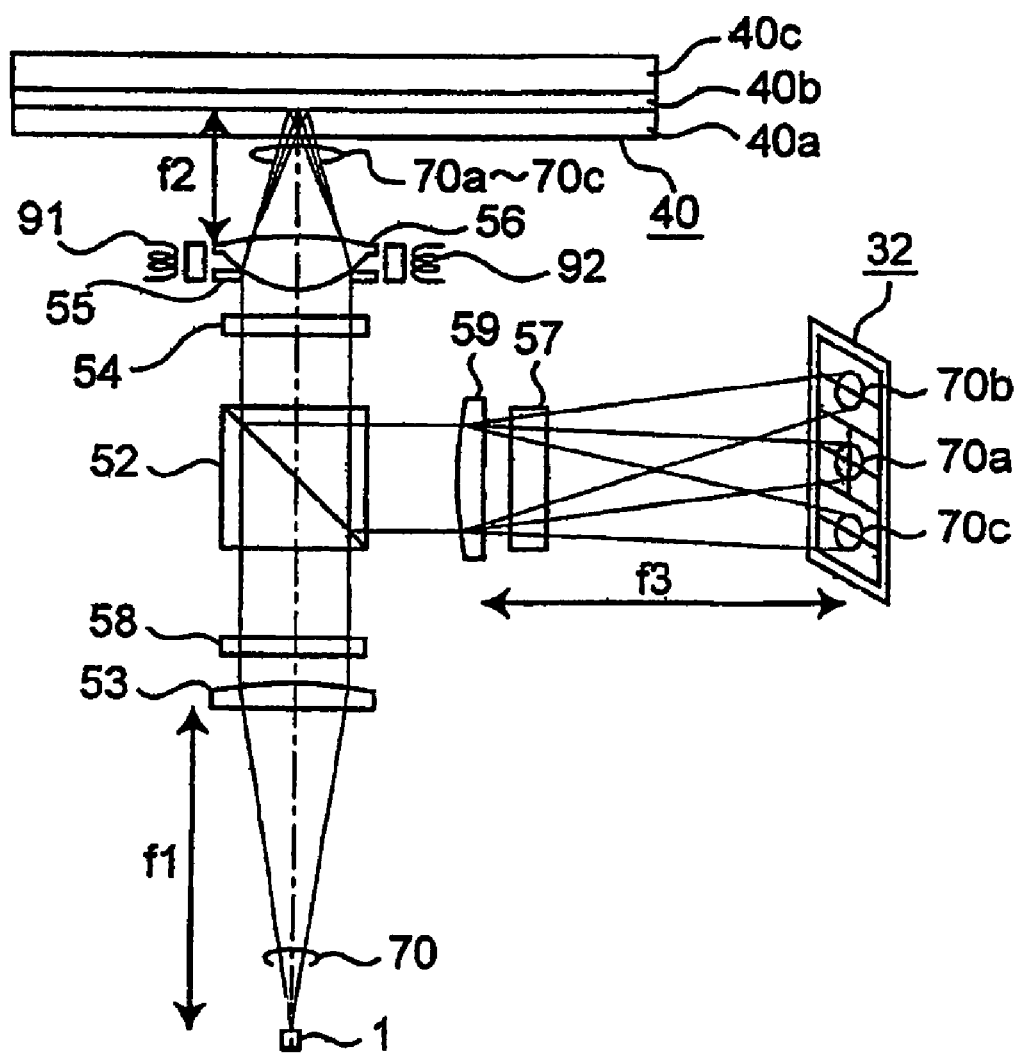
FIG. 20 is a schematic diagram of an optical pickup head in an optical disc drive according to the related art.
Figure 21:
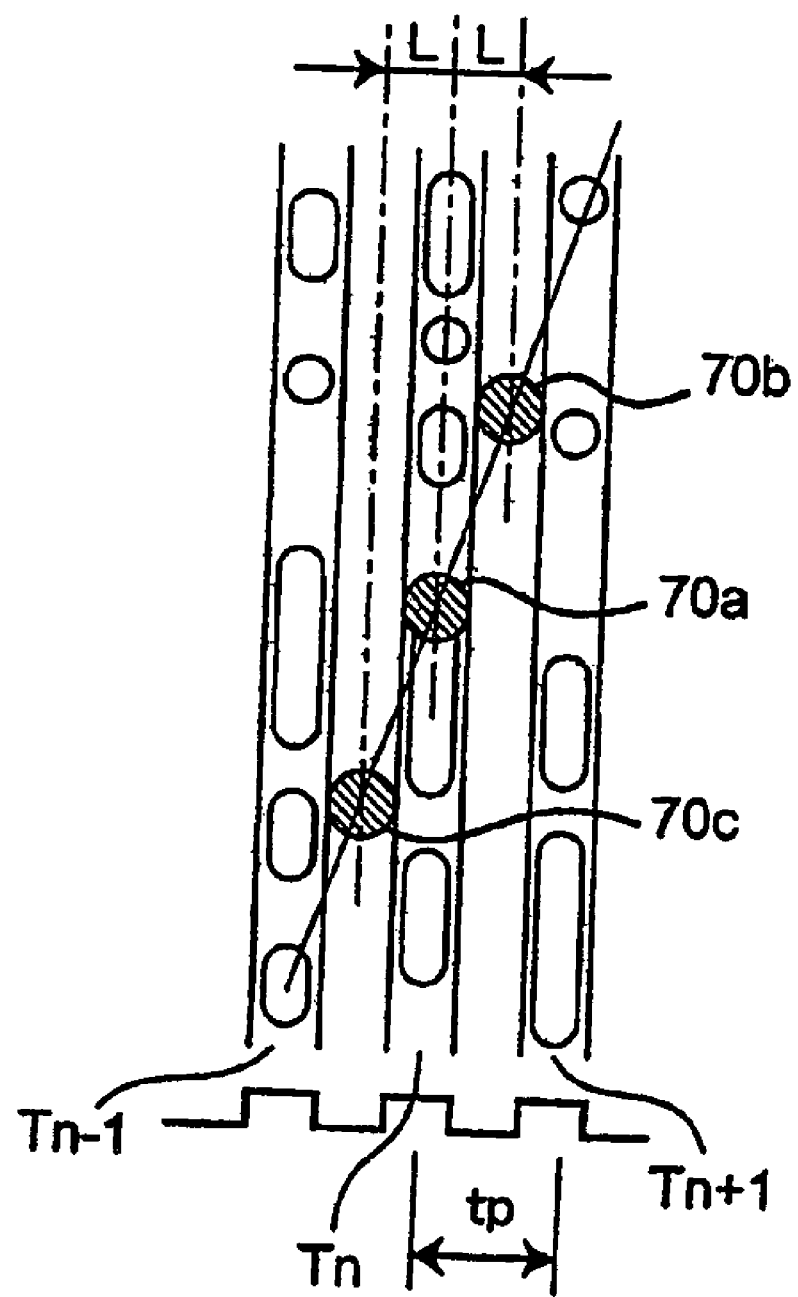
FIG. 21 shows the relationship between the beam and tracks on the optical storage medium in a conventional optical disc drive.

The operation for determining the recording power is described next. Note that the signal output from the circuits forming the apparatus shown in FIG. 9, and the recording marks formed n the optical disc 101 according to said signals, are shown in FIG. 18 and FIG. 19 and referenced below.

(a) First, the recording power setting means 109 sets initial peak power 1103, bias power 1104, and bottom power 1105 levels in laser drive circuit 108.

(b) The recording means 107 then sends to the laser drive circuit 108 a signal for continuously recording one revolution of the groove track from a specified position.

(c) The laser drive circuit 108 then sends to the optical pickup head 102 a pulse train 116 shaped according to the length of the marks to be recorded, and the signal is then recorded by the optical pickup head 102. The light output from the semiconductor laser part of the optical pickup head 102 is focused as a light spot on the optical disc 101 at this time, thus forming recording marks 1001 according to the beam waveform. The wavelength of the laser beam output by optical pickup head 102 is 405 nm, and the objective lens has a 0.85 NA.

This embodiment of the invention records 1-7 modulation data using a mark edge recording method. This means that for a base period T, seven types of marks and spaces can be formed ranging from a shortest length of 2T to a maximum length of 8T. It will also be obvious that the invention shall not be so limited and other recording methods can be used. The shortest mark in this embodiment is approximately 0.16 µm long.

When recording ends the semiconductor laser of the optical pickup head 102 emits at the playback power level to reproduce the just-recorded track, and a signal 110 that varies according to the presence of recording marks 1001 on the optical disc 101 is input as the playback signal to the playback means 103.

Figure 14:
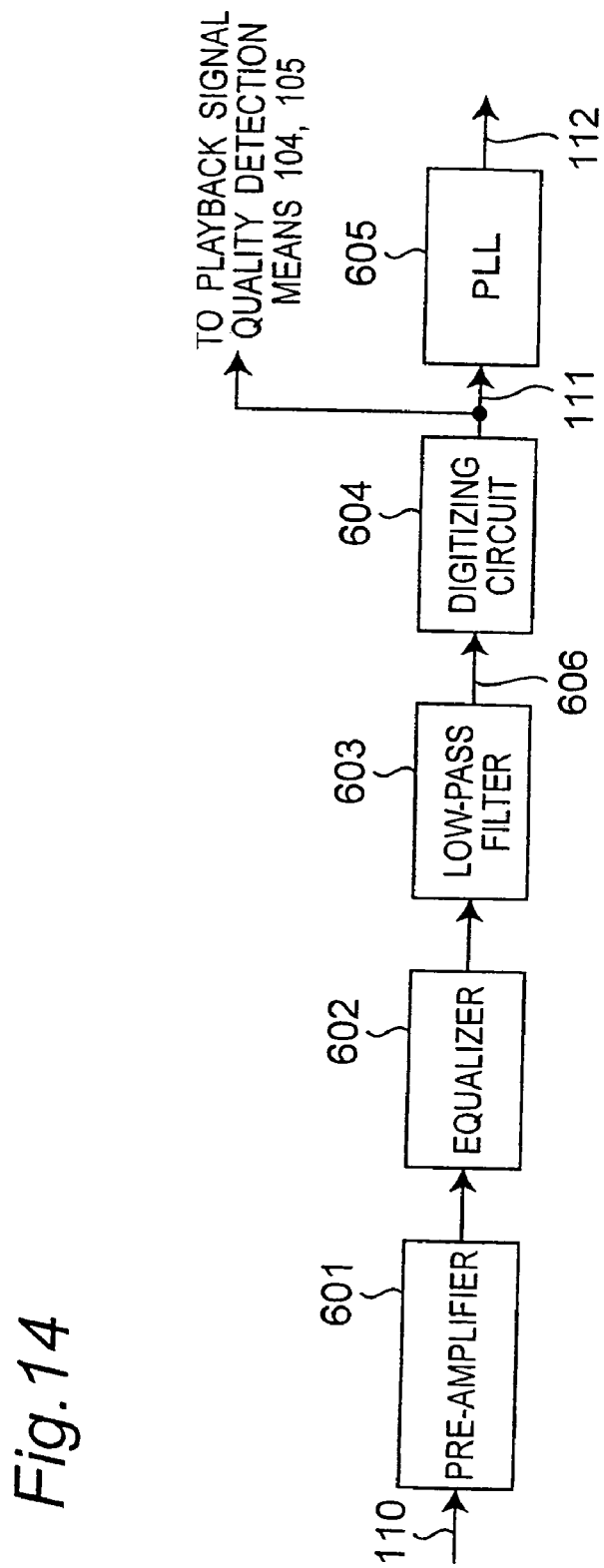
FIG. 14 is a block diagram of an optical disc drive according to a fourth embodiment of the present invention.

FIG. 14 is a block diagram showing the configuration of the playback means 103. This playback means 103 has a pre-amplifier 601, equalizer 602, low-pass filter 603, digitizing circuit 604, and PLL 605. The input signal 110 is amplified by pre-amplifier 601, shaped and equalized by equalizer 602 and low-pass filter 603, and then output as signal 606. This signal 606 is then input to digitizing circuit 604 whereby pulses are output where signal 606 crosses slice level 1002, resulting in signal 111. This slice level 1002 normally operates in a band at several 10 kHz so that the integral of the marks and the integral of the spaces is equal.

Figure 15:
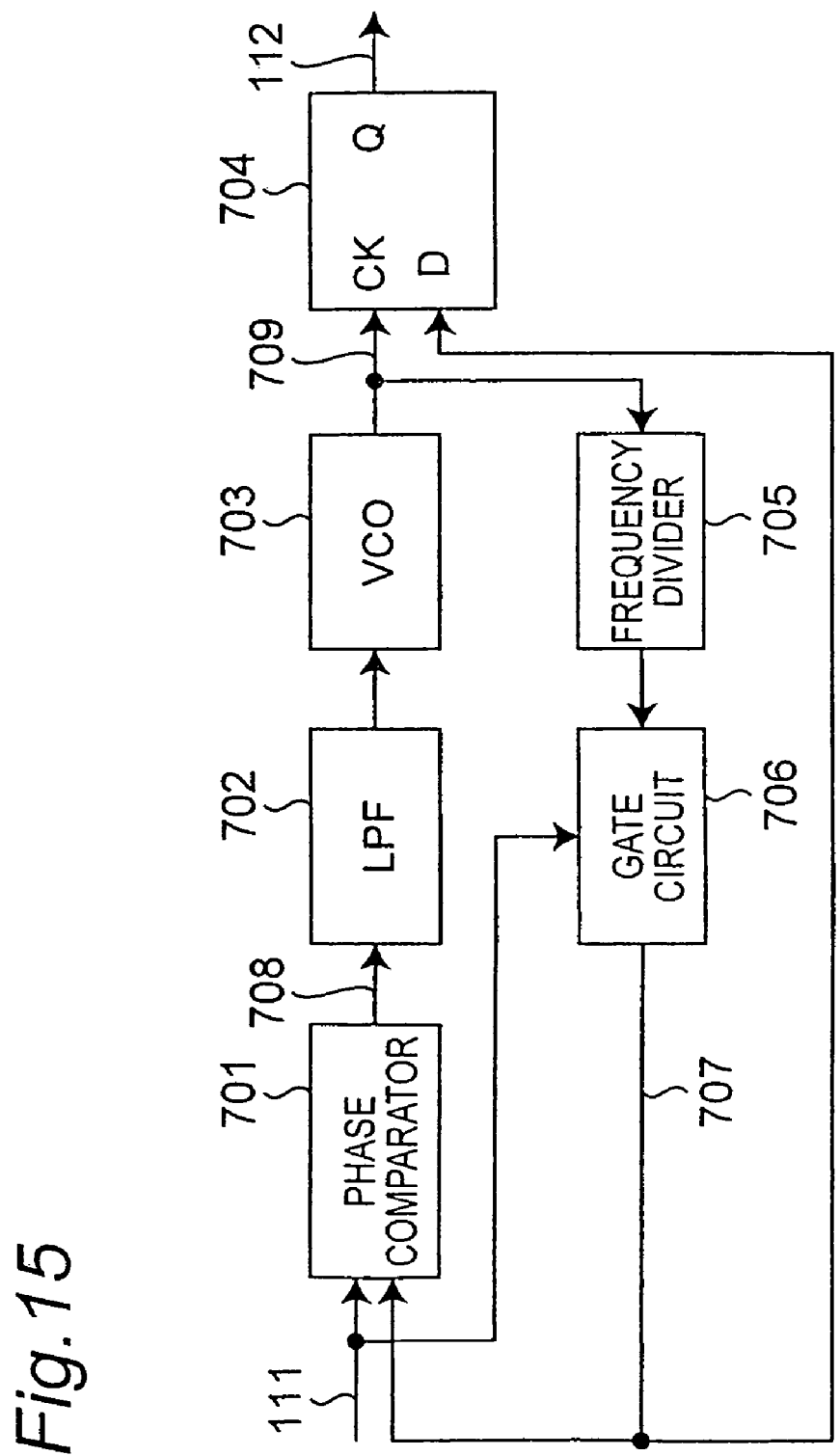
FIG. 15 is a block diagram of an optical disc drive according to a fourth embodiment of the present invention.

The output signal 111 of digitizing circuit 604 is input to PLL 605. FIG. 15 is a block diagram showing the configuration of the PLL 605. This PLL 605 has a phase comparator 701, low-pass filter 702, VCO 703, flip-flop 704, frequency divider 705, and gate circuit 706.

(a) The output signal 111 of digitizing circuit 604 is input to phase comparator 701.

(b) The phase comparator 701 detects the phase difference between input signal 111 and the output signal 707 of gate circuit 706, and outputs an error signal 708 denoting the phase difference and frequency difference between these two input signals.

(c) The low frequency component of the error signal 708 is passed by the low-pass filter 702 as the control voltage applied to the VCO 703.

(d) The VCO 703 then generates a clock signal 709 at the frequency determined by the control voltage.

(e) The clock signal 709 is frequency divided by frequency divider 705, and gate circuit 706 outputs only a signal corresponding to signal 111. The VCO 703 is controlled during this operation so that the two input signals have the same phase. As a result, signal 111 synchronized to the base period is output as signal 112 and input to playback signal quality detection means A 104 and playback signal quality detection means B 105.

Figure 16:
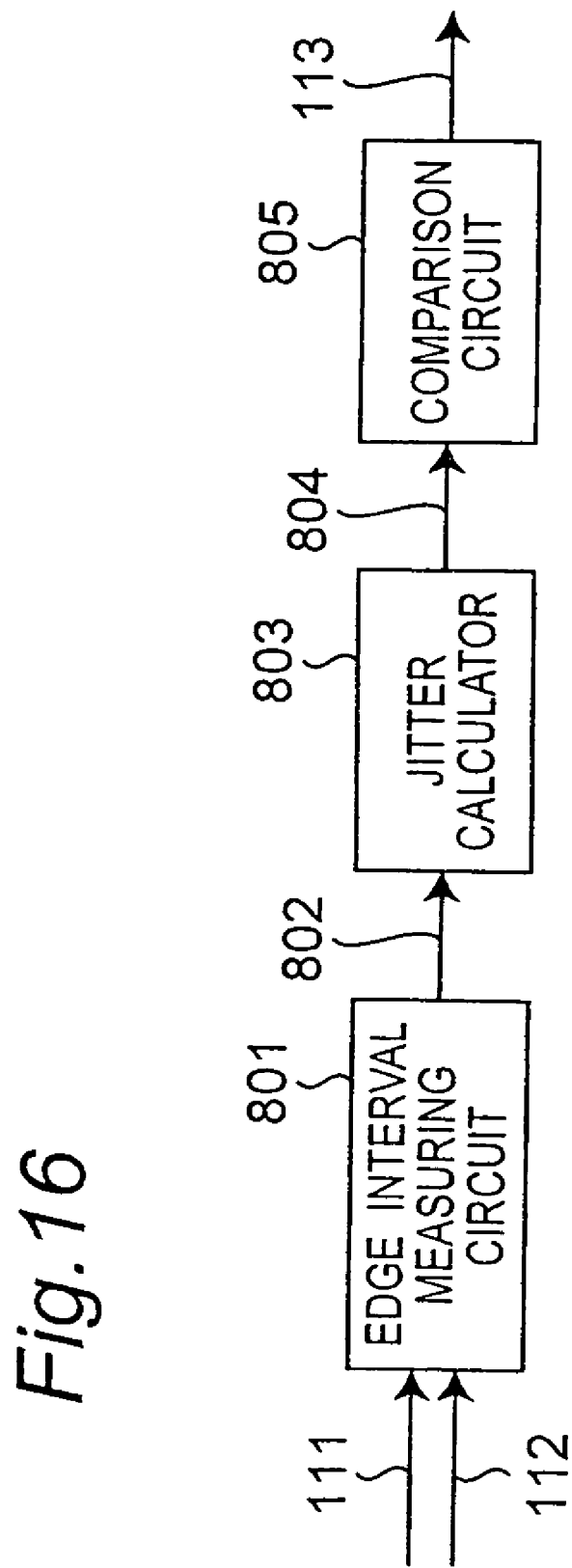
FIG. 16 is a block diagram of an optical disc drive according to a fourth embodiment of the present invention.

FIG. 16 is a block diagram of playback signal quality detection means A 104. This playback signal quality detection means A 104 has an edge interval measuring circuit 801, jitter calculator 803, and comparison circuit 805. When output signal 111 of digitizing circuit 604 and output signal 112 of PLL 605 are input to edge interval measuring circuit 801, the edge interval measuring circuit 801 measures the edge intervals t0, t1, t2, t3, t4, t5, t6, t7, t8, t9, . . . between two pulses, and the jitter calculator 803 outputs a jitter value. The comparison circuit 805 then compares this jitter value with a specified jitter level used as a threshold value, and outputs the result as signal 113 to optimal recording power determining means 106.

Figure 17:
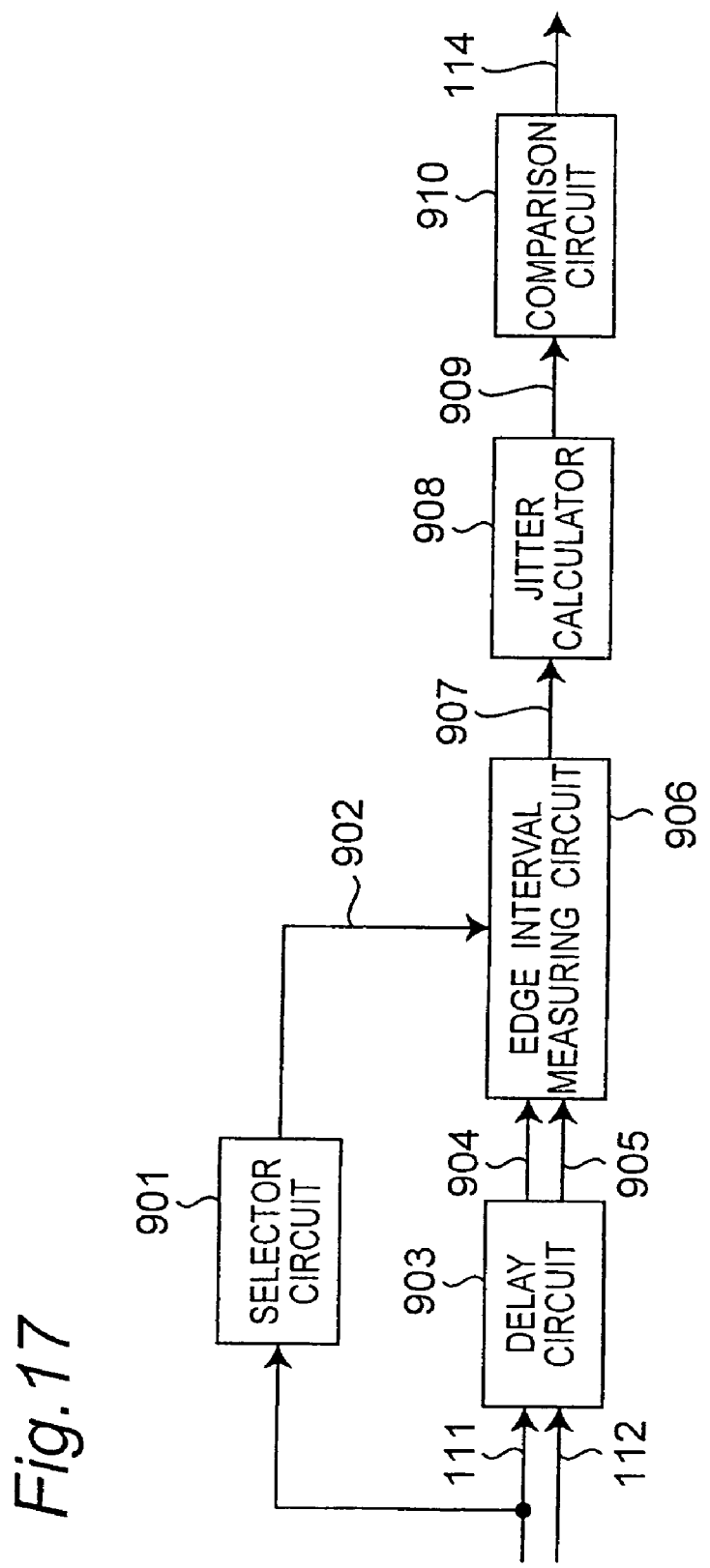
FIG. 17 is a block diagram of an optical disc drive according to a fourth embodiment of the present invention.

FIG. 17 is a block diagram of the playback signal quality detection means B 105. This playback signal quality detection means B 105 has a selector circuit 901, delay circuit 903, edge interval measuring circuit 906, jitter calculator 908, and comparison circuit 910.

(a) The output signal 111 from digitizing circuit 604 and output signal 112 of PLL 605 are input to delay circuit 903, and respective delayed signals 904 and 905 are output to edge interval measuring circuit 906.

(b) Signal 111 is also input to selector circuit 901, the edges of the shortest mark and the shortest space are detected, and the resultant signal 902 is output to edge interval measuring circuit 906. Because a 2T signal is the shortest signal in this embodiment of the invention, pulse intervals of 2T or less or (2T+a) or less are detected where a is 0.5T or less and is preferably 0.25T or less. This signal 902 is used to mask the shortest marks and spaces, which in this embodiment means masking marks and spaces of length 2T.

(c) As shown in FIG. 19 the edge interval measuring circuit 906 does not measure edge intervals t3 and t6, which are masked by signal 902, in signal 904, but does measure the edge intervals t0, t1, t2, t4, t5, t7, t8, t9, . . . between the other pulses, and jitter calculator 908 then calculates the jitter.

(d) The comparison circuit 910 then compares the calculated jitter value (909) with the specific jitter level used as a threshold value, and outputs the result as signal 114 to optimal recording power determining means 106.

Figure 11:
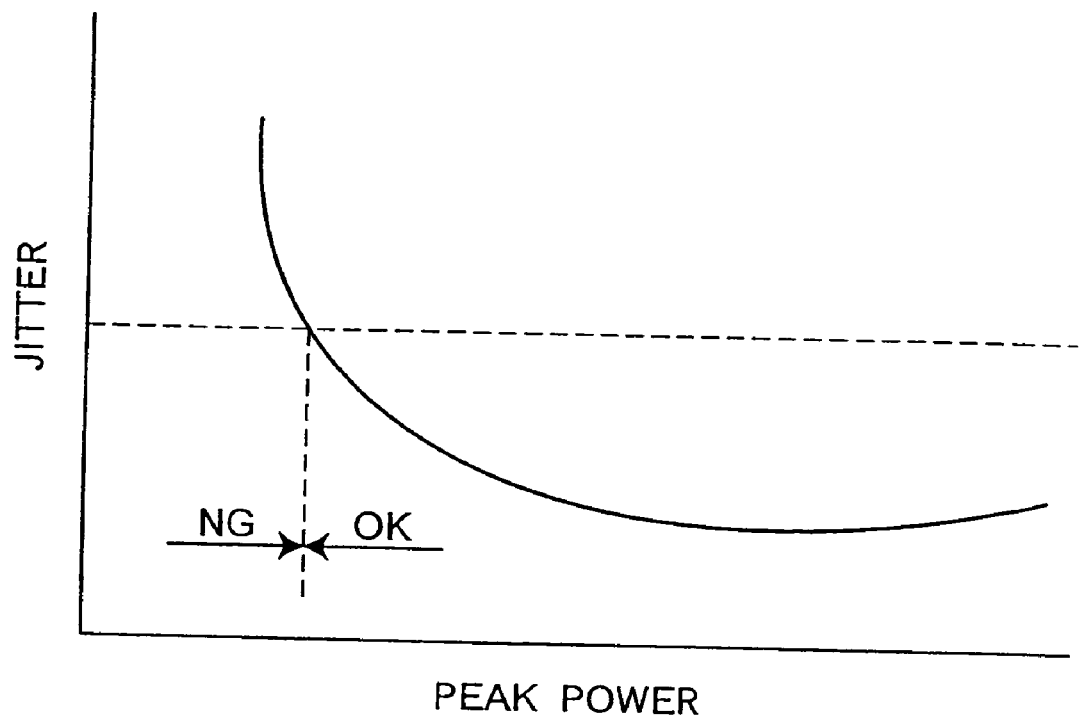
FIG. 11 shows the correlation between peak power and jitter in a fourth embodiment of the present invention.

FIG. 11 shows the relationship between peak power and jitter. Peak power is shown on the horizontal axis and jitter on the vertical axis in FIG. 11. Jitter is the temporal shift in the playback signal from the source signal, results from a drop in the playback signal amplitude due to insufficient emission power in the laser beam during recording, decreases as the playback signal amplitude increases, and remains substantially constant when the playback signal amplitude is saturated. If playback conditions are equal, less jitter indicates more accurate recording. Therefore, if jitter from the recorded is less than or equal to the threshold value, the result is OK, but if it is greater than or equal to the threshold value, the result is NG.

Figure 13:
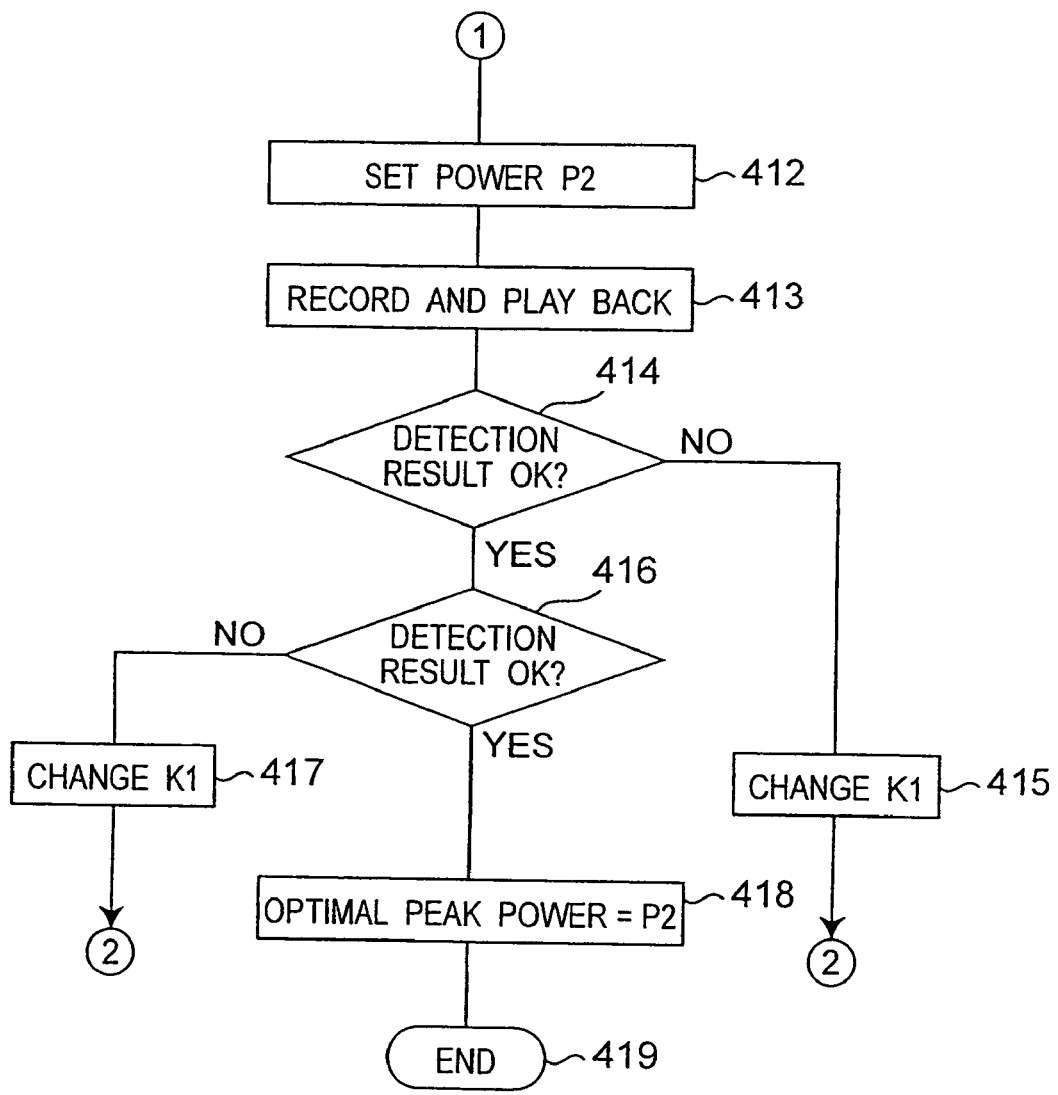
FIG. 13 is a flow chart related to a fourth embodiment of the present invention.

The optimal recording power determining means 106 operates according to a process shown, for example, in the flow charts in FIG. 12 and FIG. 13.

(a) First, if the first result returned by playback signal quality detection means A 104 is NG, peak power is set to a level above the initial setting (step 405), and if the first result is OK, peak power is set to a level below the initial setting (step 404). The groove track is then recorded and reproduced at the reset peak power level (step 406).

(b) If the first detection result returned by the playback signal quality detection means A 104 is NG and the second detection result is OK, the optimal recording power determining means 106 uses the following equation to calculate power P2, which is the average power (P1) of the first peak power setting and the second peak power setting plus a specific margin (step 411).

$P1$=(current peak power+previous peak power)/2

$P2=K1 \times P1$ (adding a margin, where $K1>1$)

(c) If the first detection result returned by the playback signal quality detection means A 104 is OK and the second detection result is NG, the optimal recording power determining means 106 uses the following equation to calculate power P2, which is the average power (P1) of the first peak power setting and the second peak power setting plus a specific margin (step 411).

$P1$=(current peak power+previous peak power)/2

$P2=K1 \times P1$ (adding a margin, where $K1>1$)

(d) If the first detection result returned by the playback signal quality detection means A 104 is OK and the second detection result is OK, peak power is set to a level lower than the peak power used for the second recording, recording is repeated at this peak power setting and playback signal quality is detected. If the third detection result from the playback signal quality detection means A 104 is NG, the optimal recording power determining means 106 calculates power P2 as the average (P1) of the second peak power and third peak power settings plus a specific margin (step 411).

(e) This peak power P2 is then set (step 412) and a random signal is recorded and reproduced using peak power P2 (step 413).

(f) The playback signal quality detection means A 104 then detects playback signal quality (step 414).

(g) If the detection result is NG, the margin coefficient K1 used in step 411 is changed (step 415), and the process repeats from step 412. If this changed margin coefficient results in an OK detection result, playback signal quality is next detected by playback signal quality detection means B 105 (step 416). If the detection result is NG, the margin coefficient K1 used in step 411 is changed (step 417), and the process repeats from step 412. If playback signal quality is OK as a result of this changed coefficient, peak power P2 is used as the peak power for recording user data (step 418). The change to coefficient K1 in step 415 is a maximum +/−10%, and in step 417 is a maximum +/−5%.

By detecting jitter from the edges of the shortest marks and spaces and detecting jitter not including from the edges of the shortest marks and spaces in order to confirm recording performance, data can be correctly recorded even when defocusing or relative tilt between the head and optical storage medium occurs during actual recording.

Furthermore, even better-optimized recording and playback is possible by setting a threshold value for jitter including the edges of the shortest marks and spaces and a threshold value for jitter not including the edges of the shortest marks and spaces.

In other words, even better-optimized recording and playback is enabled when the optical storage medium can record so as to satisfy the threshold value for jitter including the edges of the shortest marks and spaces and the threshold value for jitter not including the edges of the shortest marks and spaces. It should be noted that these threshold values could be recorded to a read-only area of the optical storage medium, or they could be stored in memory in the optical disc drive.

It will also be obvious that the preceding embodiments are described by way of example only, and the present invention can be varied in many ways without departing from the scope of the invention.

For example, leading and trailing mark edges are not distinguished for use as a jitter and error rate evaluation standards, but they could be. By identifying the leading edges and trailing edges, cases in which jitter or the error rate is particularly high at either the leading or trailing edge can be eliminated. Furthermore, if edges not including the shortest marks and spaces can be identified, the error rate could be used instead of jitter as the detected value.

Furthermore, edges including the shortest marks and spaces are detected by measuring the pulse intervals in the output signal 111 of the digitizing circuit 604, but detecting the shortest marks and spaces shall not be limited to this method. More specifically, the detection method is not specifically limited, and a method in which two threshold values SL1 and SL2 are set as shown in FIG. 3 and the shortest marks and spaces are detected from signal amplitude could be used.

Furthermore, the edge interval measuring circuit 906 does not measure edge intervals masked by the output signal 902 of selector circuit 901, but another method could be used insofar as it can measure jitter from edges not including the shortest marks and spaces.

Furthermore, edge intervals are measured based on the output signal 111 of digitizing circuit 604 and the output signal 112 of PLL 605, but edge interval measurement shall not be so limited and the edge interval could be measured for only output signal 111 of 504. If jitter in output signal 112 can be ignored, jitter in the edge intervals of the digitizing circuit 604 output signal 111 is logically approximately 1.41 times edge interval jitter based on digitizing circuit 604 output signal 111 and PLL 605 output signal 112, and adequate benefit is achieved by detecting only jitter in the edge intervals in the output signal 111 of digitizing circuit 604.

Using PRML in the playback system further improves shortest mark and shortest space detection performance. In this case detecting jitter from edges not including the shortest marks and spaces is particularly effective in the present embodiment. For example, when two recording states having equal jitter at all edges are compared, a lower jitter level from edges not including the shortest marks and spaces means that data can be reproduced more accurately. However, because of the effect of the shortest marks and spaces, edges including the shortest marks and spaces can be correctly detected as 2T marks and spaces using a PRML method even when jitter is high at all edges. As a result, data can be reproduced more accurately than when jitter from all edges is low.

Furthermore, the coding system shall not be limited to a shortest mark length of 2T, and the same effect can be achieved whether the shortest mark length is 3T, 1T, or other length.

By recording marks so as to minimize variation in edges not including the shortest marks and spaces, data can be correctly reproduced when a PRML method is used even if jitter for all edges is high if the marks are recorded with sufficient amplitude to enable detecting whether or not a signal is present even when the shortest marks and spaces are not recorded at the correct time interval. As a result, determining the recording conditions by detecting jitter for edges not including the shortest marks and spaces as in the present embodiment is therefore extremely effective.

Furthermore, this embodiment detects both jitter from edges not including the shortest marks and spaces and jitter from edges including the shortest marks and spaces, but adequate performance is achieved even when only jitter for edges not including the shortest marks and spaces is detected.

Yet further, adequate performance is achieved whether jitter is detected for edges not including the shortest marks and spaces, or whether jitter is detected only for edges not including the shortest marks or for edges not including the shortest spaces.

Furthermore, even if a PRML method is not used, the shortest mark length is known in the case of RLL coding, and the shortest marks and spaces can be easily detected. More specifically, if RLL(1,7) modulation is used and a 2.5T signal is detected from the playback waveform, the signal could be a 2T or 3T signal, but a 2T signal is likely if a signal shorter than 2T is detected. Detecting jitter from edges not including the shortest marks and spaces as described in the present embodiment is therefore effective when RLL coding is used for recording.

The jitter level used as the threshold value will vary according to the error correction capability of the optical disc drive and the type of equalizer. Assuming an optical disc drive with a bit error rate of $1.0 \times 10-4$ to $1.0 \times 10-3$ before error correction, however, a level of approximately 8% to 11% is preferable in playback signal quality detection means A 104 using a normal linear equalizer as used in this embodiment of the invention, and a level of approximately 6% to 9% is preferable using a nonlinear equalizer, such as a limit equalizer in which signal boost is greater than in a linear equalizer. Likewise in playback signal quality detection means B 105, 7% to 10% is preferable with a normal linear equalizer as in the present embodiment, and 5% to 8% is preferable with a nonlinear equalizer, such as a limit equalizer in which signal boost is greater than in a linear equalizer. The jitter level used for the threshold value in playback signal quality detection means A 104 is greater than or equal to the jitter level used as the threshold value in playback signal quality detection means B 105. The jitter level can vary 1-2% according to the configuration of the playback channel.

The period for continuous recording and continuous playback shall also not be limited, and recording by either sector unit or ECC block could be used in an optical disc drive that records by sector unit.

Test recording shall also not be limited to one revolution of the recording track. Five tracks, for example, could be continuously recorded and the middle track then reproduced. This better simulates actual recording conditions by including erasure from adjacent tracks, and can therefore detect jitter under conditions closer to actual data recording conditions.

The tracks on each side of a center track could also be recorded after recording the center track. This assures that the effect of erasure from adjacent tracks is also included in jitter detection, and enables detecting jitter under conditions closer to the actual data recording conditions. Considering different data recorded to an adjacent track by a different optical disc drive, the adjacent tracks can be recorded at a peak power setting higher than the peak power level to record the center track. Higher reliability recording is enabled by determining the peak power level under more stringent conditions.

If the effect of recording to adjacent tracks on the center track is not particularly considered, the center track can be recorded after recording the adjacent tracks. This reduces the effect of the adjacent tracks when the track pitch is not uniform, and can thus determine the correct peak power setting.

Recording shall also not be limited to once to the same track, and the same track could, for example, be recorded ten times. By recording multiple times to an optical storage medium that can be written multiple times, jitter can be detected under conditions that are even closer to the actual data recording conditions. Jitter can be detected every time data is recorded, in which case the optimal peak power can be determined with consideration for the initial overwrite characteristic of the optical storage medium.

Furthermore, in order to record multiple times and overwrite an area recorded at a high peak power level by a different optical disc drive, data can be overwritten at the peak power used to record the user area after recording at a peak power level higher than the peak power used to record the user area. By determining the peak power under more stringent conditions, data can be recorded with higher reliability.

These embodiments have been described with reference to the peak power setting, but the bias power and bottom power can be determined using the same method used to determine the peak power, and can be changed with reference to the peak power setting.

The present invention shall also not be limited to the above-described track configuration, and can be applied to optical storage media that record to land tracks as well as optical storage media that record to both land tracks and groove tracks.

The optical storage media could also have one recording layer, two recording layers, or more recording layers. With a two-layer optical storage medium, for example, the effect of coma aberration from the laser beam is less and the tilt characteristic is better in the layer closer to the optical pickup head than the farther layer. As a result, the threshold value for detecting jitter from edges including the shortest marks and spaces and the threshold value for detecting jitter for edges not including the shortest marks and spaces can be set higher for the layer closer to the optical pickup head than the layer farther from the head. Setting the threshold jitter value for edges including the shortest marks and spaces and the threshold jitter value for edges not including the shortest marks and spaces separately for each layer enables recording and playback optimized for each layer. Furthermore, these threshold values can be recorded to a read-only area of the optical storage medium, or stored in memory in the optical disc drive.

Furthermore, the parameter that is changed according to the result of playback signal quality detection shall not be limited to a power setting, and could, for example, determine the width of position of the pulse train shaped according to the length of the recorded mark.

Furthermore, jitter is not only caused by the recording conditions. Jitter also results from variation in the recording marks as a result of such factors during recording as unoptimized laser emission power due to tilt or defocusing, and fluctuation in the emission power itself. Jitter could also result from fluctuation in the playback signal due to noise in the playback device, tilt, or defocusing even though there is little variation in the recording marks themselves.

The optical storage medium of this invention is also not limited to phase-change media, and the invention applies to any optical storage medium that uses RLL coding, including various types of magneto-optical storage media. Read-only optical storage media could also be used. By detecting jitter for edges including both the shortest marks and spaces and detecting jitter for edges not including the shortest marks and spaces in the optical storage media performance verification step of the read-only media production process, data can be reproduced more reliably during actual use even if defocusing or relative tilt between the optical pickup head and optical storage medium occurs.

As described above, the present invention provides an optical storage medium, optical disc drive, optical storage medium inspection apparatus, and optical storage medium inspection method that can reduce the effect of increased jitter when using an optical storage medium in which jitter is increased due to marks being formed at smaller than the desired size, and that can highly reliably record and reproduce data even when defocusing or relative tile between the optical storage medium and head occurs during recording or playback.

The invention shall not be limited to the embodiments described in the scope of the accompanying claims, and can also be achieved as described below.

A first version of the invention is an optical disc drive having an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium using two threshold values. The optical storage medium has a recording layer for recording data. Digital data of length kT based on a period T is recorded as a mark and space sequence to the recording layer, k is an integer of 2 or more, and the width of a 2T mark is narrower than the width of a 3T or longer mark.

A second version is an optical disc drive having an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium using maximum likelihood decoding. The optical storage medium has a recording layer for recording data. Digital data of length kT based on a period T is recorded as a mark or space sequence to the recording layer, k is an integer of 2 or more, and the width of a 2T long digital data mark is narrower than the width of a digital data mark longer than 2T.

A third version is an optical disc drive having an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium using two threshold values. The optical storage medium has a first recording layer and a second recording layer. The first recording layer is a semi-transparent layer that passes part of the light incident thereon, light passing the first recording layer reaches the second recording layer, and digital data of length kT based on a period T is recorded as a mark or space sequence to the first recording layer, k being an integer of 2 or more.

A fourth version is an optical disc drive having an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium using maximum likelihood decoding. The optical storage medium has a first recording layer and a second recording layer. The first recording layer is a semi-transparent layer that passes part of the light incident thereon; light passing the first recording layer reaches the second recording layer, and digital data of length kT based on a period T is recorded as a mark or space sequence to the first recording layer, k being an integer of 2 or more.

A fifth version is an optical disc drive having an optical pickup head that emits a light beam to the optical storage medium, detects the light beam reflected from the optical storage medium, and outputs a signal based on the received reflected light; a clock generating means for receiving signals output from the optical pickup head and extracting digital information recorded to the optical storage medium; and a demodulation means that reproduces data recorded to the optical storage medium. The optical storage medium has a first recording layer and a second recording layer. The first recording layer is a semi-transparent layer that passes part of the light incident thereon; light passing the first recording layer reaches the second recording layer, and digital data of length kT based on a period T is recorded as a mark or space sequence to the first recording layer, k being an integer of 2 or more. The clock generating means generates a clock signal by treating as invalid signals obtained from the edges of 2T digital data marks or spaces.

A sixth version is an optical disc drive having an optical pickup head that emits a light beam to the optical storage medium, detects the light beam reflected from the optical storage medium, and outputs a signal based on the received reflected light; a clock generating means for receiving signals output from the optical pickup head and extracting digital information recorded to the optical storage medium; and a demodulation means that reproduces data recorded to the optical storage medium. The optical storage medium has a recording layer. Digital data of length kT based on a period T is recorded as a mark or space sequence to the recording layer, k is an integer of 2 or more, and the width of a 2T digital data mark is narrower than the width of a digital data mark longer than 2T. The clock generating means generates a clock signal by treating as invalid signals obtained from the edges of 2T digital data marks or spaces.

A seventh version is an optical disc drive having an optical pickup head that emits a light beam to the optical storage medium, detects the light beam reflected from the optical storage medium, and outputs a signal based on the received reflected light; a clock generating means for receiving signals output from the optical pickup head and extracting digital information recorded to the optical storage medium; a demodulation means that reproduces data recorded to the optical storage medium; and a TE signal generating means used for tracking control. The optical storage medium has a recording layer. Digital data of length kT based on a period T is recorded as a mark or space sequence to the recording layer, k being an integer of 2 or more. The tracking error signal generating means generates a tracking error signal from change in the signals produced when the light beam strikes the edges of the mark or space sequence recorded to the optical storage medium, and generates the tracking error signal by invalidating signal change resulting from the light beam at the edges of 2T-long digital data marks or spaces.

An eighth version of the invention is an optical disc drive in which the recording layer of the optical storage medium enables repeatedly recording and erasing information.

A ninth version of the invention is an optical disc drive in which the recording layer of the optical storage medium can be recorded only once.

A tenth version of the invention is an optical disc drive in which the recording layer of the optical storage medium is read-only.

An eleventh version of the invention is an optical disc drive in which the first recording layer of the optical storage medium is read-only and the second recording layer can be recorded only once.

A twelfth version of the invention is an optical disc drive in which the first recording layer of the optical storage medium is read-only and the second recording layer can be repeatedly recorded and erased.

A thirteenth version of the invention is an optical disc drive having an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium. The optical storage medium has a recording layer for recording data. Digital data of length kT based on a period T is recorded as a mark or space sequence to the recording layer, k is an integer of 2 or more, and the width of a 2T digital data mark is narrower than the width of a 3T or longer digital data mark. The optical disc drive adjusts the length of a 2T digital data mark so that the length detected from a pattern repeatedly recording 2T-long digital data marks and spaces goes to the same level as a threshold value suitable for reproducing information in a pattern repeatedly recording 3T or longer digital data marks and spaces.

A fourteenth version of the invention is an optical disc drive having an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium. The optical storage medium has a recording layer for recording data. Digital data of length kT based on a period T is recorded as a mark or space sequence to the recording layer, and k is an integer of 2 or more. The optical disc drive has an evaluation standard so that mark and space length is appropriate, and adjusts the length of digital data marks and spaces longer than 2T so that the length is appropriate relative to the evaluation standard.

A fifteenth version of the invention is an optical disc drive having an optical pickup head that emits a light beam to the optical storage medium, detects the light beam reflected from the optical storage medium, and outputs a signal based on the received reflected light; and a demodulation means that receives the signal output from the optical pickup head and reproduces information recorded to the optical storage medium. The optical storage medium has a recording layer for recording data, and digital data of length kT based on a period T is recorded as a mark or space sequence to the recording layer using an evaluation standard for adjusting mark and space length to an appropriate length. When recording to an optical storage medium that is normally recorded with k being an integer of 2 or more, the optical disc drive records information using a k of 3 or more, and adjusts the length of digital data marks and spaces of length 3T or more so that the length is appropriate relative to the evaluation standard.

A sixteenth version of the invention is an optical disc drive where the evaluation standard is jitter.

A seventeenth version of the invention is an optical disc drive where the evaluation standard is an error rate.

An eighteenth version of the invention is an optical disc drive where the evaluation standard is the time period of an obtained signal.

A nineteenth version of the invention is an optical disc drive whereby mark length is adjusted by adjusting the power of the laser beam emitted from the optical pickup head.

A twentieth version of the invention is an optical disc drive whereby mark length is adjusted by adjusting the pulse width of the laser beam emitted from the optical pickup head.

A twenty-first version of the invention is an optical disc drive that measures jitter from an optical storage medium where the width of 2T-long digital data marks is narrower than the width of digital data marks longer than 2T.

A twenty-second version of the invention is an optical disc drive that measures jitter in a signal obtained by emitting a light beam to the first recording layer of an optical storage medium having a first recording layer and a second recording layer, the first recording layer being a semi-transparent film that passes part of the light incident thereon, the light passing the first recording layer reaching the second recording layer.

A twenty-third version of the invention is an optical disc drive where a signal reproduced from a pattern repeatedly recording 2T-long digital data marks and spaces is 12 pp, a signal reproduced from a pattern repeatedly recording 8T-long digital data marks and spaces is 18 pp, and 12 pp/18 pp<0.2.

A twenty-fourth version of the invention is an optical disc drive where the length of a pair of digital data marks and spaces of length 2T is ML, the wavelength of the light beam emitted from the optical pickup head is $\lambda$, the numeric aperture of the collector optics of the optical pickup head is NA, and $ML<\lambda/(1.25*NA)$.

A twenty-fifth version of the invention is an optical disc drive further comprising a gain adjustment means so that variation in the amplitude of signals input to the demodulation means is small when the reflectivity of the optical storage medium varies.

A twenty-sixth version of the invention is an optical storage medium whereby information is recorded or reproduced by exposure to a light beam, the optical storage medium having a first recording layer and a second recording layer as recording layers for recording information, the first recording layer being a read-only recording layer, the second recording layer being a recording layer enabling recording data only once, and the first recording layer being disposed closer to the light incidence side of the medium than the second recording layer.

A twenty-seventh version of the invention is an optical storage medium whereby information is recorded or reproduced by exposure to a light beam, the optical storage medium having a first recording layer and a second recording layer as recording layers for recording information, the first recording layer being a read-only recording layer, the second recording layer being a recording layer enabling repeatedly recording and erasing data, and the first recording layer being disposed closer to the light incidence side of the medium than the second recording layer.

A twenty-seventh version of the invention is an optical storage medium having multiple tracks formed concentrically or in a spiral for recording information using marks and spaces between the marks by emitting a light beam to the recording surface of the tracks, and is characterized by a signal not including edges adjacent to the shortest marks and/or the shortest spaces denoting a first playback signal quality.

A twenty-eighth version of the invention is an optical storage medium characterized by a signal including edges adjacent to the shortest marks and/or the shortest spaces denoting a second playback signal quality.

A twenty-ninth version of the invention is an optical storage medium characterized by the first playback signal quality being higher than the second playback signal quality.

A thirtieth version of the invention is an optical storage medium characterized by jitter being detected as the playback signal quality.

A thirty-first version of the invention is an optical storage medium characterized by distinguishing leading-edge jitter and trailing-edge jitter.

A thirty-second version of the invention is an optical storage medium characterized by an error rate being detected as the playback signal quality.

A thirty-third version of the invention is an optical storage medium characterized by having multiple recording layers and setting playback signal quality for each layer.

A thirty-fourth version of the invention is an optical storage medium characterized by the quality of the layer farthest from the optical pickup head during recording being highest.

A thirty-fifth version of the invention is an optical storage medium characterized by the playback signal quality threshold value being written to a specific area of the optical storage medium.

A thirty-sixth version of the invention is an optical storage medium characterized by the specific area being a read-only area.

A thirty-seventh version of the invention is an optical storage medium characterized by signals also being recorded to tracks adjacent to a track having a specified playback signal quality.

A thirty-eighth version of the invention is an optical storage medium characterized by the track having a specified playback signal quality being recorded before recording to the adjacent tracks.

A thirty-ninth version of the invention is an optical storage medium characterized by the emission power of the laser beam when recording the adjacent tracks being greater than the emission power of the laser beam when recording the track having a specified playback signal quality.

A fortieth version of the invention is an optical storage medium characterized by the track having a specified playback signal quality being recorded after recording to one adjacent track.

A forty-first version of the invention is an optical storage medium characterized by the track having a specified playback signal quality being recorded after recording to both adjacent tracks.

A forty-second version of the invention is an optical storage medium characterized by the track having a specified playback signal quality being recorded multiple times.

A forty-third version of the invention is an optical storage medium characterized by having a specified playback signal quality in all of a specific number of recordings.

A forty-fourth version of the invention is an optical storage medium characterized by recording at a second emission power level after recording at a first emission power level, the first emission power level being higher than the second emission power level.

A forty-fifth version of the invention is an optical disc drive for reading an optical storage medium having multiple tracks formed concentrically or in a spiral for recording information using marks and spaces between the marks by emitting a light beam to the recording surface of the tracks, the optical storage medium having a first playback signal quality denoted by a signal not including edges adjacent to the shortest marks and/or the shortest spaces.

A forty-sixth version of the invention is an optical disc drive for reading an optical storage medium having multiple tracks formed concentrically or in a spiral for recording information using marks and spaces between the marks by emitting a light beam to the recording surface of the tracks, the optical storage medium having a first playback signal quality denoted by a signal not including edges adjacent to the shortest marks and/or the shortest spaces, and a second playback signal quality denoted by a signal including edges adjacent to the shortest marks and/or the shortest spaces.

A forty-seventh version of the invention is an optical disc drive for recording so that a signal not including edges adjacent to the shortest marks and/or the shortest spaces has a first playback signal quality, the optical disc drive characterized by comprising means for recording a signal, means for reproducing the recorded signal, means for detecting a shortest mark or a shortest space in the reproduced signal, and a playback signal quality detection means for detecting playback signal quality in a signal not including edges adjacent to the detected shortest mark or shortest space.

A forty-eighth version of the invention is an optical disc drive wherein a signal including edges adjacent to the shortest marks and/or the shortest spaces denotes a second playback signal quality.

A forty-ninth version of the invention is an optical disc drive wherein the first playback signal quality is higher than the second playback signal quality.

A fiftieth version of the invention is an optical disc drive that detects jitter as playback signal quality.

A fifty-first version of the invention is an optical disc drive that distinguishes leading-edge jitter and trailing-edge jitter.

A fifty-second version of the invention is an optical disc drive that detects an error rate as playback signal quality.

A fifty-third version of the invention is an optical disc drive that sets playback signal quality for each recording layer of an optical storage medium having multiple recording layers.

A fifty-fourth version of the invention is an optical disc drive wherein the quality of the layer farthest from the optical pickup head during recording is highest.

A fifty-fourth version of the invention is an optical disc drive wherein the playback signal quality threshold value is written to a specific area of the optical disc drive.

A fifty-fifth version of the invention is an optical disc drive wherein signals are also recorded to tracks adjacent to a track having a specified playback signal quality.

A fifty-sixth version of the invention is an optical disc drive wherein the track having a specified playback signal quality is recorded before recording to the adjacent tracks.

A fifty-seventh version of the invention is an optical disc drive wherein the emission power of the laser beam when recording the adjacent tracks is greater than the emission power of the laser beam when recording the track having a specified playback signal quality.

A fifty-eighth version of the invention is an optical disc drive wherein the track having a specified playback signal quality is recorded after recording to one adjacent track.

A fifty-ninth version of the invention is an optical disc drive wherein the track having a specified playback signal quality is recorded after recording to both adjacent tracks.

A sixtieth version of the invention is an optical disc drive wherein the track having a specified playback signal quality is recorded multiple times.

A sixty-first version of the invention is an optical disc drive having a specified playback signal quality in all of a specific number of recordings.

A sixty-second version of the invention is an optical disc drive characterized by recording at a second emission power level after recording at a first emission power level, the first emission power level being higher than the second emission power level.

A sixty-third version of the invention is an optical disc drive characterized by determining emission power for recording according to the detected playback signal quality.

A sixty-fourth version of the invention is an optical disc drive wherein the emission power is determined in an area outside the user area for recording user data.

Although the present invention has been described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart therefrom.

The invention claimed is:

1. An optical storage medium inspection method for determining if an optical storage medium is good or defective, said method comprising:
    emitting a light beam from an optical pickup head to the optical storage medium to which digital information is recorded as a train of marks or spaces of length kT based on a period T and an integer k;
    receiving light reflected by a mark or space;
    measuring jitter in signals based on the reflected light, but not measuring jitter in signals obtained from edges of shortest marks or spaces; and
    determining from the measured jitter whether the optical storage medium is good or defective.

* * * * *